US009358302B2

(12) United States Patent
Avci et al.

(10) Patent No.: US 9,358,302 B2
(45) Date of Patent: Jun. 7, 2016

(54) GLYCOCONJUGATE VACCINES

(75) Inventors: Fikri Avci, Boston, MA (US); Dennis L. Kasper, Boston, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 13/258,722

(22) PCT Filed: Jan. 8, 2010

(86) PCT No.: PCT/US2010/020536
§ 371 (c)(1),
(2), (4) Date: Nov. 21, 2011

(87) PCT Pub. No.: WO2010/110931
PCT Pub. Date: Sep. 30, 2010

(65) Prior Publication Data
US 2012/0064108 A1    Mar. 15, 2012

Related U.S. Application Data

(60) Provisional application No. 61/162,619, filed on Mar. 23, 2009.

(51) Int. Cl.
*A61K 39/00* (2006.01)
*A61K 47/48* (2006.01)
*C07K 1/107* (2006.01)

(52) U.S. Cl.
CPC ......... *A61K 47/4833* (2013.01); *A61K 47/4823* (2013.01); *C07K 1/1077* (2013.01); *A61K 39/00* (2013.01)

(58) Field of Classification Search
None
See application file for complete search history.

(56) References Cited

U.S. PATENT DOCUMENTS

| | | | |
|---|---|---|---|
| 6,027,733 A | 2/2000 | Wang et al. | |
| 6,274,144 B1 | 8/2001 | Wang et al. | |
| 6,669,945 B1 | 12/2003 | Nardin et al. | |
| 6,855,321 B1 | 2/2005 | Rappuoli et al. | |
| 2004/0022840 A1* | 2/2004 | Nagy et al. | 424/450 |
| 2006/0024669 A1 | 2/2006 | Bogoch et al. | |
| 2008/0112951 A1 | 5/2008 | Phalipon et al. | |
| 2008/0220030 A1 | 9/2008 | Fernandez et al. | |

FOREIGN PATENT DOCUMENTS

| | | |
|---|---|---|
| JP | 2008-533108 | 8/2008 |
| JP | 2008-542342 | 11/2008 |
| WO | 96/40795 | 12/1996 |
| WO | 03-094959 | 11/2003 |
| WO | 2005/003775 | 1/2005 |
| WO | 2006/097558 | 9/2006 |
| WO | 2008/041703 | 10/2008 |
| WO | 2008/157590 | 12/2008 |

OTHER PUBLICATIONS

James et al (International Immunology 19(11):1291-1301, 2007).*
Falugi et al (European Journal of Immunology, 31:3816-1824, 2001).*
Abdel et al., "Immunization with glycosylated Kb-binding peptides generates carbohydrate-specific, unrestricted cytotoxic T cells," Eur. J. Immunol., 26:544-551 (1996).
Amir-Kroll et al., "A conjugate vaccine composed of a heat shock protein 60 T-cell epitope peptide (p458) and Neisseria meningitidis type B capsular polysaccharide," Vaccine, 24:6555-6563 (2006).
Amir-Kroll et al., "Proteins and their derived peptides as carriers in a conjugate vaccine for Streptococcus pneumoniae: self-heat shock protein 60 and tetanus toxoid," Journal of Immunology, 170:6165-6171 (2003).
Arnold et al., "Substrate specificity of cathepsins D and E determined by N-terminal and C-terminal sequencing of peptide pools," Eur. J. Biochem., 249:171-179 (1997).
Barrett, "Human immune responses to polysaccharide antigens: an analysis of bacterial polysaccharide vaccines in infants," Adv. Pediatr., 32:139-158 (1985).
Bixer et al., "Synthetic Peptide Representing a T-Cell Epitope of CRM197 Substitutes as Carrier Molecule in a Haemophilus Influenzae type B (HIB) Conjugate Vaccine," Immunobiology of Proteins and Peptides V Vaccines, pp. 175-180 (1989).
Cobb et al., "Polysaccharide processing and presentation by the MHCII pathway," Cell, 117:677-687 (2004).
Cohen et al., "Pneumococcal capsular polysaccharide is immunogenic when present on the surface of macrophages and dendritic cells: TLR4 signaling induced by a conjugate vaccine or by lipopolysaccharide is conducive," J. Immunol., 180:2409-2418 (2008).
Conus and Simon, "Cathepsins: key modulators of cell death and inflammatory responses," Biochemical Pharmacology, 76:1374-1382 (2008).
Corthay et al., "Cathepsins: key modulators of cell death and inflammatory responses," Eur. J. Immunol., 28:2580-2590 (1998).
Coutinho et al., "In vitro activation of mouse lymphocytes in serum-free medium: effect of T and B cell mitogens on proliferation and antibody synthesis," Eur. J. Immunol., 3:299-306 (1973).
Coutinho, "B cell mitogenic properties of thymus-independent antigens," Nature New Biol., 245:12-14 (1973).
De Jong et al., "Blocking inducible co-stimulator in the absence of CD28 impairs Th1 and CD25+ regulatory T cells in murine colitis," Int. Immunol., 16(2):205-213 (2004).
De Velasco et al., "Synthetic peptides representing T-cell epitopes act as carriers in pneumococcal polysaccharide conjugate vaccines," Infect. Immun., 63:961-968 (1995).
Dong et al., "ICOS co-stimulatory receptor is essential for T-cell activation and function," 409(6816):97-101 (2001).
Dormitzer et al., "Structure-based antigen design: a strategy for next generation vaccines," Trends Biotechnol., 26(12):659-667 (2008).

(Continued)

*Primary Examiner* — Patricia Duffy
(74) *Attorney, Agent, or Firm* — Fish & Richardson P.C.

(57) ABSTRACT

Glycoconjugate vaccines and methods of preparing and using the same are described.

42 Claims, 13 Drawing Sheets

(56) References Cited

OTHER PUBLICATIONS

Duan et al., "Microbial carbohydrate depolymerization by antigen-presenting cells: deamination prior to presentation by the MHCII pathway," Proc. Natl. Acad. Sci. USA, 105(13):5183-5188 (2008).
Dzhambazov et al., "The major T cell epitope on type II collagen is glycosylated in normal cartilage but modified by arthritis in both rats and humans," Eur. J. Immunol., 35:357-366 (2005).
Dziadek et al., "A novel linker methodology for the synthesis of tailored conjugate vaccines composed of complex carbohydrate antigens and specific TH-cell peptide epitopes," Chem. Eur. J., 14:5908-5917 (2008).
Elinger et al., "Use of prior vaccinations for the development of new vaccines," Science, 249:423-425 (1990).
Falugi et al., "Rationally designed strings of promiscuous CD4(+) T cell epitopes provide help to Haemophilus influenzae type b oligosaccharide: a model for new conjugate vaccines," Eur. J. Immunol., 31:3816-3824 (2001).
Guttormsen et al., "Immunologic memory induced by a glycoconjugate vaccine in a murine adoptive lymphocyte transfer model," Infect. Immun., 66:2026-2032 (1998).
Guttormsen et al., "Cognate stimulatory B-cell-T-cell interactions are critical for T-cell help recruited by glycoconjugate vaccines," Inf. Imm., 67(12):6375-6384 (1999).
Hanish and Ninkovic, "Immunology of O-glycosylated proteins: approaches to the design of a MUC1 glycopeptide-based tumor vaccine," Curr. Protein and Peptide Sci., 7:307-315 (2006).
Haurum et al., "Recognition of carbohydrate by major histocompatibility complex class I-restricted, glycopeptide-specific cytotoxic T lymphocytes," J. Exp. Med., 180:739-744 (1994).
Hudrisier et al., "Genetically encoded and post-translationally modified forms of a major histocompatibility complex class I-restricted antigen bearing a glycosylation motif are independently processed and co-presented to cytotoxic T lymphocytes," J. Biol. Chem., 274:36274-36280 (1999).
International Search Report as issued in PCT/US2010/020536 on Sep. 14, 2010.
Jensen et al., "Carbohydrate and peptide specificity of MHC class II-restricted T cell hybridomas raised against an O-glycosylated self peptide," J. Immunol., 158:3769-3778 (1997).
Johnson et al., "Canine vaccine recipients recognize an immunodominant region of the rabies virus glycoprotein," Journal of General Virology, 83:2663-2669 (2002).
Jones, Vaccines based on the cell surface carbohydrates of pathogenic bacteria, Anais da Academia Brasileira de Ciências, 77(2):293-324 (2005).
Kaliyaperumal et al., "Carrier-induced epitope-specific regulation and its bypass in a protein-protein conjugate," Eur. J. Immunol., 25:3375-3380 (1995).
Kalka-Moll et al., "Effect of molecular size on the ability of zwitterionic polysaccharides to stimulate cellular immunity," J. Immunol., 164:719-724 (2000).
Kasper et al., "Immune response to type III group B streptococcal polysaccharide-tetanus toxoid conjugate vaccine," J. Clin. Invest., 98:2308-2314 (1996).
Könen-Waisman et al., "Self heat-shock protein (hsp60) peptide serves in a conjugate vaccine against a lethal pneumococcal infection," J. Inf. Dis., 179:403-413 (1999).
Kumar et al., ""Universal" T helper cell determinants enhance immunogenicity of a Plasmodium falciparum merozoite surface antigen peptide," J. Immunology, 148:1499-1505 (1992).
Langenberg, "A recombinant glycoprotein vaccine for herpes simplex virus type 2: safety and immunogenicity [corrected]," Ann. Int. Med., 122(12):889-898 (1995).
Lesinski and Westerink, "Novel vaccine strategies to T-independent antigens," J. Microbiol. Methods, 47:135-149 (2001).
Lesinski and Westerink, "Vaccines against polysaccharide antigens," Curr. Drug Targets Infect. Disord., 1:325-334 (2001).
Mazmanian et al., "An immunomodulatory molecule of symbiotic bacteria directs maturation of the host immune system," Cell, 122:107-118 (2005).
McFarland et al., "Ovalbumin(323-339) peptide binds to the major histocompatibility complex class II I-A(d) protein using two functionally distinct registers," Biochemistry, 38:16663-16670 (1999).
McGhee et al., Microbial. Immunol., 28:261-280 (1984).
Michaelson et al., "Identification of an immunodominant type-II collagen peptide recognized by T cells in H-2q mice: self tolerance at the level of determinant selection," Eur. J. Immunol., 22:1819-1825 (1992).
Mitchison, "The carrier effect in the secondary response to hapton-protein conjugates; II Cellular cooperation," Eur. J. Immunol., 1:18-25 (1971).
Nikaido, "Structure and functions of the cell envelope of gram-negative bacteria," Rev. Infect. Dis., 10:S279-S281 (1988).
Paoletti and Madoff, "Vaccines to prevent neonatal GBS infection," Semin. Neonatol., 7:315-323 (2002).
Paoletti et al., "An oligosaccharide-tetanus toxoid conjugate vaccine against type III group B *Streptococcus*," J. Biol. Chem., 265(30):18278-18283 (1990).
Paoletti et al., "Effects of alum adjuvant or a booster dose on immunogenicity during clinical trials of group B streptococcal type III conjugate vaccines," Infect. Immun., 69:6696-6701 (2001).
Paoletti et al., "Glycoconjugate vaccines to prevent group B streptococcal infections," Expert Opin. Biol. Ther., 3:975-984 (2003).
Paoletti et al., "Group B *Streptococcus* type II polysaccharide-tetanus toxoid conjugate vaccine," Infect. Immun., 60:4009-4014 (1992).
Paoletti et al., "Neonatal mouse protection against infection with multiple group B streptococcal serotypes by maternal immunization with a tetravalent GBS polysaccharide-tetanus toxoid conjugate vaccine," Infect. Immun., 62:3236-3243 (1994).
Perez-Melgosa et al., "Carrier-mediated enhancement of cognate T cell help: the basis for enhanced immunogenicity of meningococcal outer membrane protein polysaccharide conjugate vaccine," Eur. J. Immunol., 31:2373-2381 (2001).
Plüger et al., "Specific role for cathepsin S in the generation of antigenic peptides in vivo," Eur. J. Immunol., 32:467-476 (2002).
Purcell et al., "More than one reason to rethink the use of peptides in vaccine design," Nat. Rev. Drug Disc., 6:404-414 (2007).
Riniker et al., "A General Strategy for the Synthesis of Large Peptides: The Combined Solid-Phase and Solution Approach," Tetrahedron, 49(41):9307-9320 (1993).
Roberts, "Lysosomal cysteine proteases: structure, function and inhibition of cathepsins," Drug News Perspect., 18(10):605 (2005).
Ruigrok and Gerlier, "Structure of the measles virus H glycoprotein sheds light on an efficient vaccine," PNAS, 104(52):20639-20640 (2007).
Ruiz-Perez et al., "Modulation of surgical fibrosis by microbial zwitterionic polysaccharides," PNAS, 102:16753-16758 (2005).
Sadd et al., "Bypass of carrier-induced epitope-specific suppression using a T-helper epitope," Immunology, 76:599-603 (1992).
Shelly et al., "Comparison of pneumococcal polysaccharide and CRM197-conjugated pneumococcal oligosaccharide vaccines in young and elderly adults," Inf. Immun., 65:242-247 (1997).
Siber et al., "Pneumococcal disease: prospects for a new generation of vaccines," Science, 265(5177):1385-1387 (1994).
Sood et al., "Capsular polysaccharide-protein conjugate vaccines and intravenous immunoglobulins," Expert Opin Investig. Drugs, 7:333-347 (1988).
Vafai, "Boosting immune response with a candidate varicella-zoster virus glycoprotein subunit vaccine," Vaccine, 13(14):1336-1338 (1995).
Valmori et al., "Use of Human universally antigenic tetanus toxin T cell epitopes as carriers for human vaccination," J. Immunol., 149:717-721 (1992).
Vella et al, "Immunogenicity of conjugate vaccines consisting of pneumococcal capsular polysaccharide types 6B, 14, 19F, and 23F and a meningococcal outer membrane protein complex," Inf. Immun., 60:4977-4983 (1992).
Vlad et al., "Complex carbohydrates are not removed during processing of glycoproteins by dendritic cells: processing of tumor antigen MUC1 glycopeptides for presentation to major histocompatibility complex class II-restricted T cells," J. Exp. Med., 196:1435-1446 (2002).

(56) References Cited

OTHER PUBLICATIONS

Vliegenthart et al., "Carbohydrate based vaccines," FEBS Letters, 580:2945-2950 (2006).

Wang et al., "A bacterial carbohydrate links innate and adaptive responses through Toll-like receptor 2," J. Exp. Med., 203:2853-2863 (2006).

Wang, "Toward oligosaccharide- and glycopeptide-based HIV vaccines," Current Opinion in Drug Discovery & Development, 9(2):194-206 (2006).

Weintraub, "Immunology of bacterial polysaccharide antigens," Carbohydr. Res., 338:2539-2547 (2003).

Werdelin et al., "Processing of glycans on glycoprotein and glycopeptide antigens in antigen-presenting cells," Proc. Natl. Acad. Sci. USA, 99:9611-9613 (2002).

Xu et al., "Designer glycopeptides for cytotoxic T cell-based elimination of carcinomas," J. Exp. Med., 199(5):707-716 (2004).

Xu et al., "Synthesis and immunochemical studies on a Candida albicans cluster glycoconjugate vaccine," Org. Biomol. Chem., 5(21):3477-3485 (2007).

Xu et al., "Water-soluble pH-responsive dendritic core-shell nanocarriers for polar dyes based on poly(ethylene imine)," Macromol. Biosci., 7:968-974 (2007).

Written Opinion issued in PCT/US2010/020536 on Sep. 14, 2010 (6 pages).

Shen et al., "Preparation and preclinical evaluation of experimental group B *Streptococcus* type III polysaccharide-cholera toxin B subunit conjugate vaccine for intranasal immunization," Vaccine, 19(7-8):850-861 (2000).

Paradiso et al., "Novel Approaches to the Development of Glycoconjugate Vaccines with Synthetic Peptides as Carriers," Vaccine Research, 2(4):239-248 (1993).

Zou et al., "Preparation of Glycoconjugate Vaccines," Carbohydrate-Based Vaccines and Immunotherapies; Wiley Series in Drug Discovery and Development, John Wiley & Sons, Inc., Hoboken, New Jersey, pp. 55-88 (2009).

Avci et al., "A mechanism for glycoconjugate vaccine activation of the adaptive immune system and its implications for vaccine design," Nature Medicine, 17(12):1602-1609 (2011).

European Search Report issued in EP10756513 on Mar. 31, 2015 (14 pages).

English translation of Office Action issued in corresponding Japanese application JP2012-502024 on May 12, 2015 (3 pages).

* cited by examiner

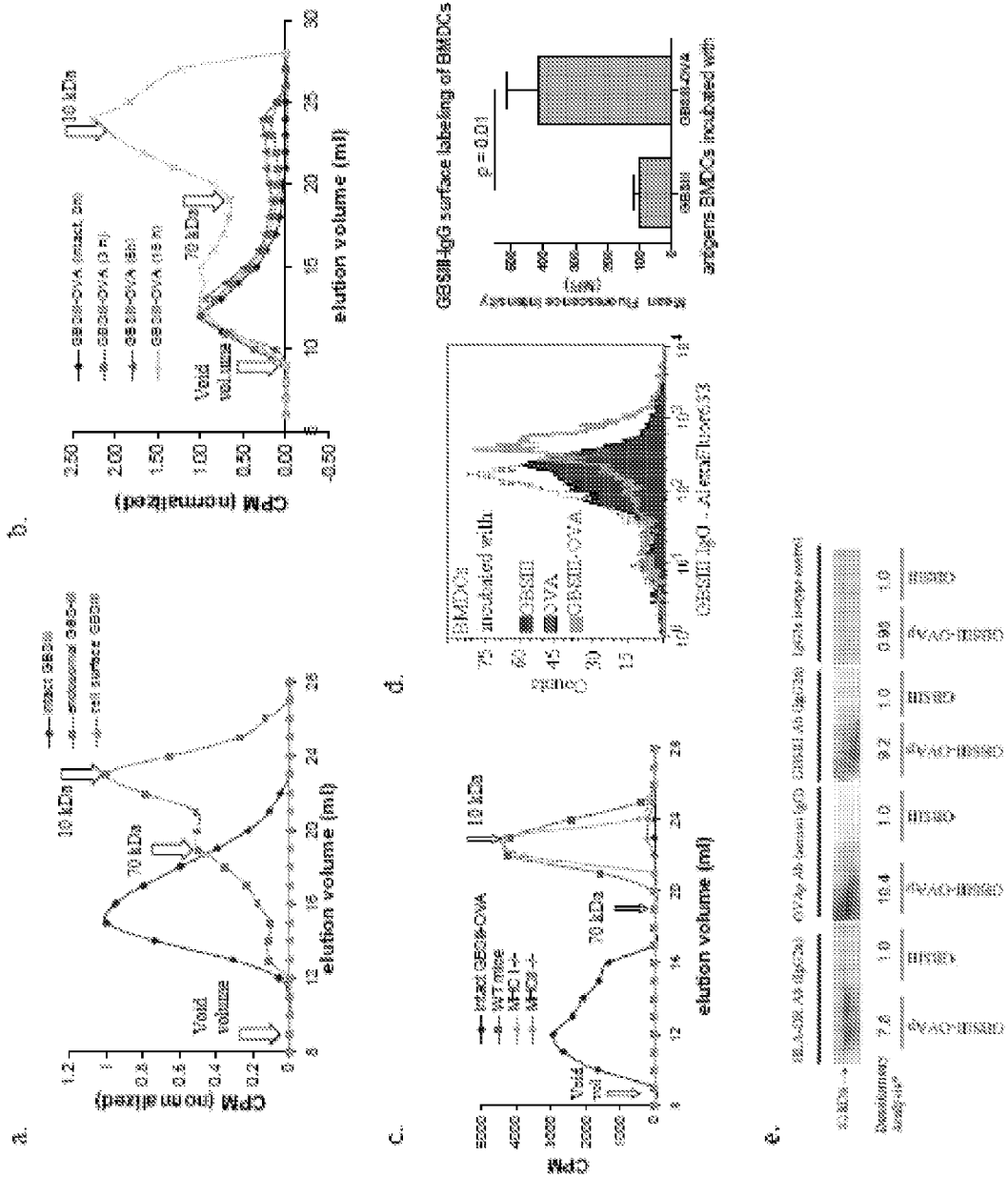
FIGURES 2A-E

FIGURES 3A-B
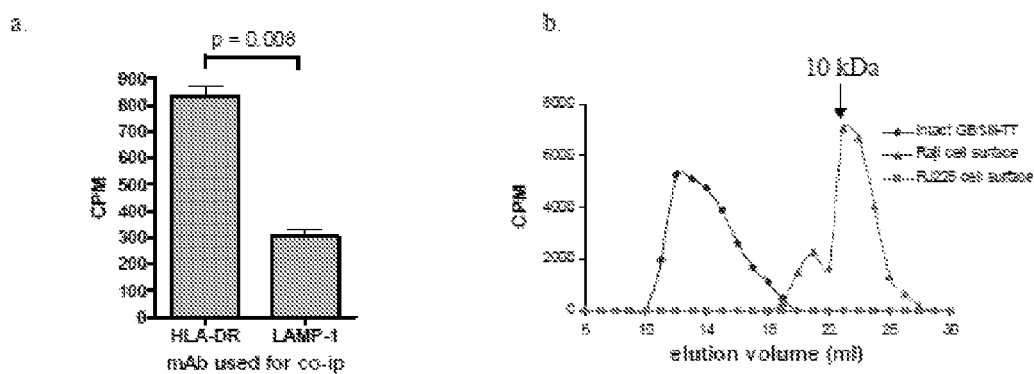
FIGURE 4A
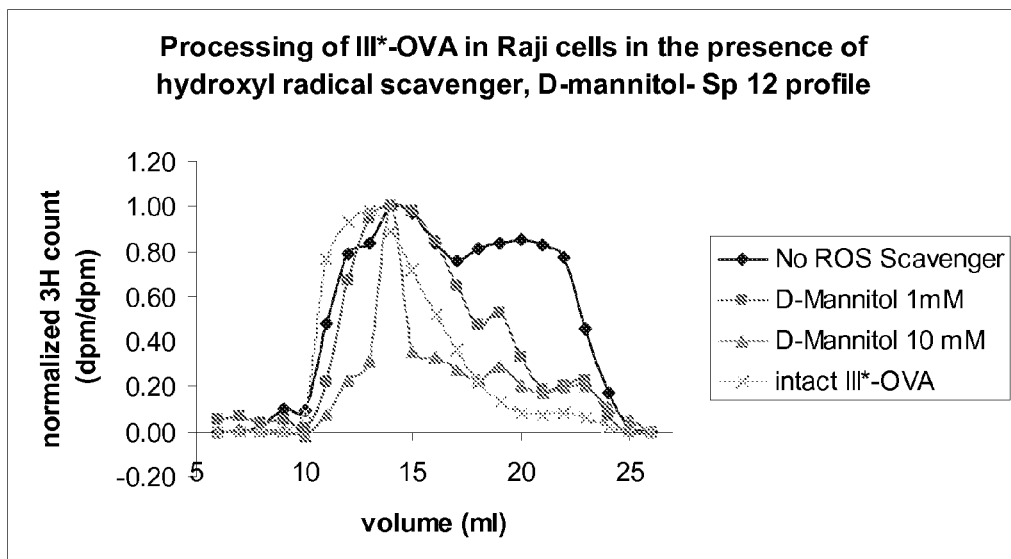

FIGURES 6A-E
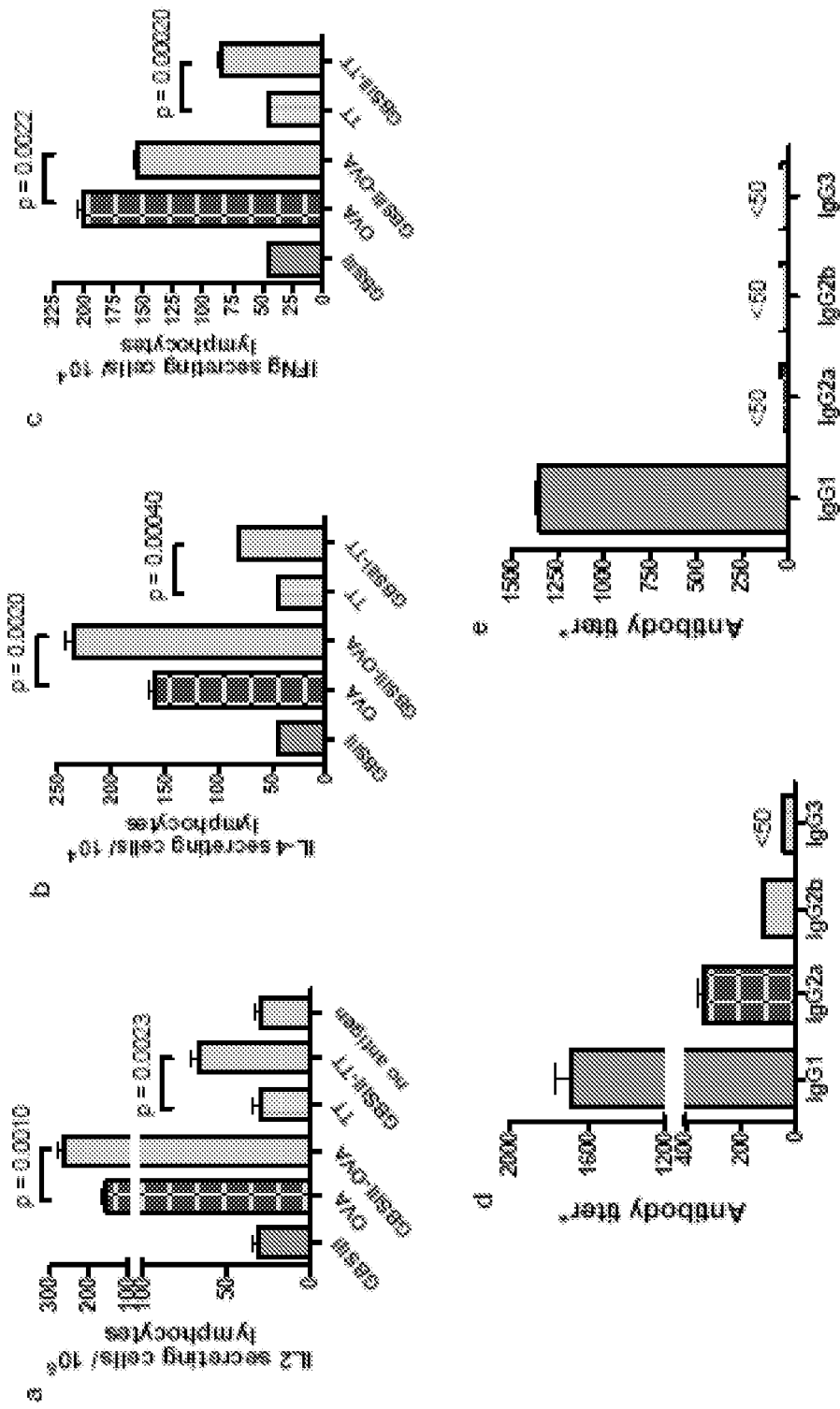

FIGURES 7A-D
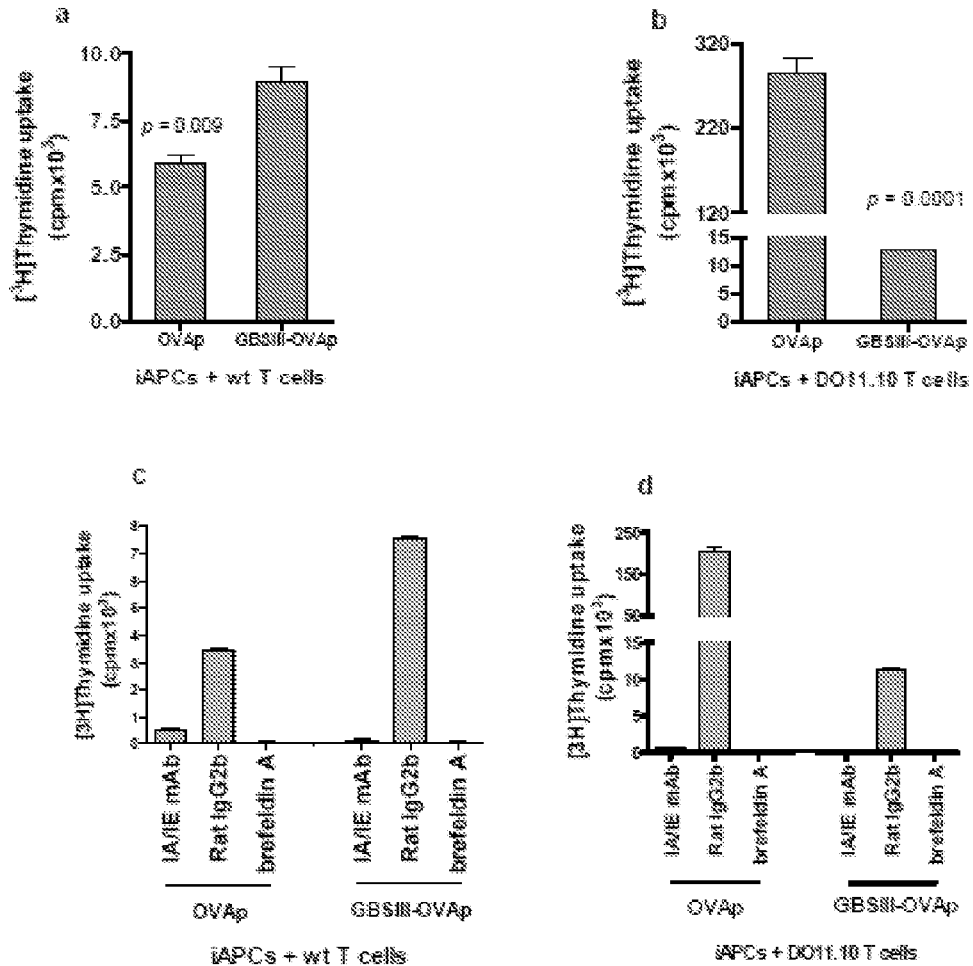
FIGURES 8A-C
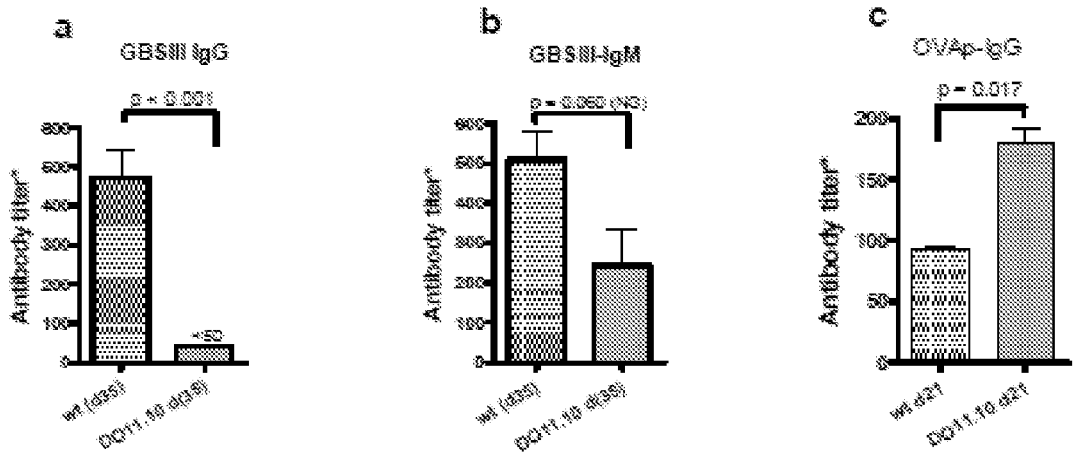

FIGURES 10A-C

FIGURES 14A-B
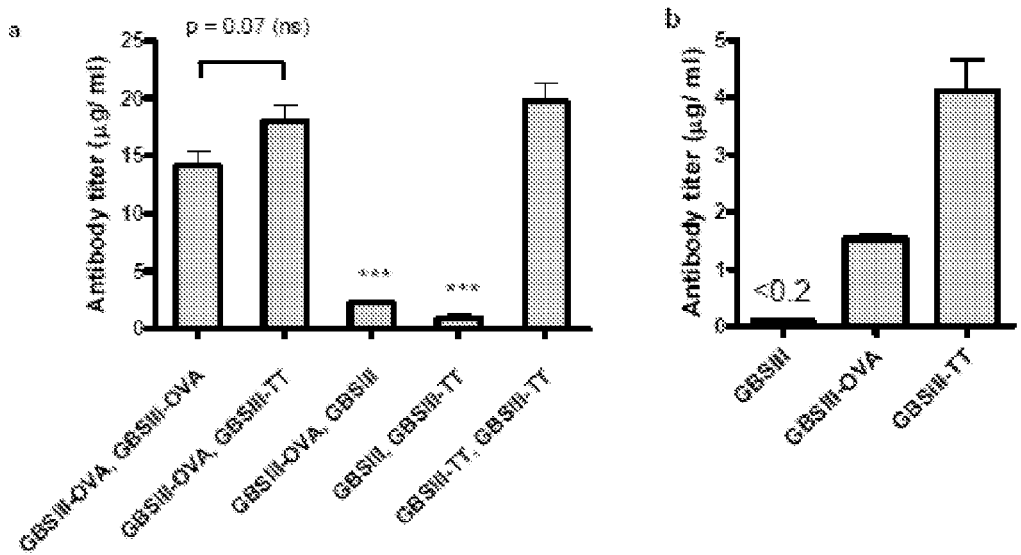
FIGURE 15A
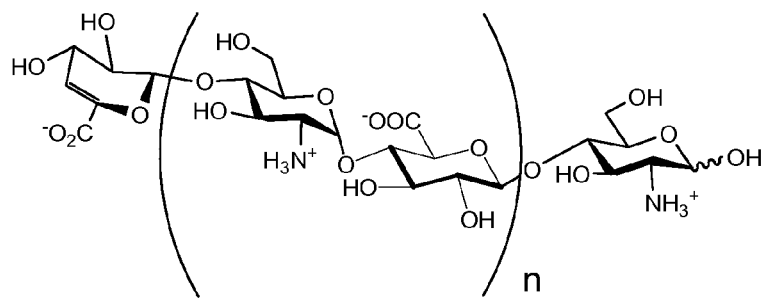
n=1, tetrasaccahride
n=2, hexasaccahride
n=3, octasaccharide
n=4, decasaccahride
n=5, dodecasaccharide
n=6, tetradecasaccharide
n~50, K5 polysaccharide

Human T Cell Assay for ZPS-oligosaccharides

GLYCOCONJUGATE VACCINES

CROSS-REFERENCE TO RELATED APPLICATION

This application is a 371 application of International Application No. PCT/US2010/020536, filed on Jan. 8, 2010, and claims the benefit of U.S. Provisional Application No. 61/162,619 filed on Mar. 23, 2009. All of the foregoing are incorporated by reference herein in their entireties.

TECHNICAL FIELD

This invention relates to glycoconjugates, e.g., glycoconjugate vaccines.

BACKGROUND

Most pathogenic bacteria elaborate large-molecular-weight (large-MW) surface polysaccharides, usually in the form of a capsule that coats and surrounds the bacterial surface. These surface carbohydrates offer substantial protection to bacterial pathogens against phagocytosis by migrating phagocytes and tissue-fixed macrophages—cells constituting a crucial host defense mechanism that limits microbial growth and spread and that probably accounts for much of the host's ability to avert microbe-induced diseases (Janeway et al., *Immunobiology*, 6th edition, Garland Science Publishing. New York, 2005). Specific polysaccharide structures function in different ways to affect bacterial interactions with the immune system and represent a paradigm for the way fine structures of carbohydrates can dictate the characteristics—and indeed the very nature—of immune responses.

Several decades ago, studies in mice showed that carbohydrates are T cell-independent antigens. Barrett, *Adv. Pediatr.*, 32:139-158 (1985); Coutinho, *Nature New Biol.*, 245:12-14 (1973); Coutinho et al., *Eur J Immunol*, 3:299-306 (1973); Guttormsen et al., *Infect Immun*, 67:6375-6384 (1999); McGhee et al., *Microbial Immunol.*, 28:261-280 (1984). Purified polysaccharides induce specific IgM responses, with minimal IgG switching. A failure to induce immunoglobulin class switching from IgM to IgG isotypes and a lack of increased antibody production after rechallenge with antigen are hallmarks of a classic T cell-independent immune response. The conjugation of polysaccharides to proteins to allow carbohydrate-specific responses that elicit T-cell help has improved the efficacy of vaccines. See Guttormsen et al., supra; Sood et al., *Expert Opin Investig Drugs*, 7:333-347 (1988). The current generation of glycoconjugate vaccines has been one of the great success stories in the biomedical sciences: in most immunized populations, infections with *Haemophilus influenzae* type b, the vaccine types of *Streptococcus pneumoniae* in children, and *Neisseria meningitidis* (except group B) have been nearly eliminated. Lesinski and Westerink, *Curr, Drug Targets Infect. Disord.*, 1:325-334 (2001); Weintraub, *Carbohydr. Res.*, 338:2539-2547 (2003).

The current mechanistic paradigm is that protective responses to glycoconjugate vaccines are based on a "trick" played on the immune system. Guttormsen et al., supra; Lesinski and Westerink, *J. Microbiol. Methods*, 47:135-149 (2001). Presumably, a B cell that is specific for production of anti-polysaccharide antibodies takes up the glycoconjugate and presents a peptide from the covalently linked protein to T cells that recognize the peptide in the context of the MHC molecule. Stimulation of the B cell (with consequent production of carbohydrate-specific antibody) and activation of the peptide-recognizing CD4$^+$ T cell result in T-cell help, which promotes immunoglobulin class switching to IgG and memory responses. Immunoglobulin class switching and B-cell memory depend on co-stimulation of the B cell through CD80 and/or CD86 interacting with CD28, through CD40 interacting with the CD40 ligand, and likely through interactions with other co-stimulatory molecules.

T cells are, however, able to recognize carbohydrates. There have been several reports on glycopeptide processing and MHC I/II presentation and recognition by T cells. Abdel et al., *Eur J Immunol*, 26:544-551 (1996); Corthay et al., *Eur J Immunol*, 28:2580-2590 (1998); Dong et al., *Nature*, 409 (6816):97-101 (2001); Dzhambazov et al., *Eur J Immunol*, 35:357-366 (2005); Hanish and Ninkovic, *Curr Protein and Peptide Sci*, 7:307-315 (2006); Haurum et al., *J Exp Med*, 180:739-744 (1994); Hudrisier et al., *J Biol Chem*, 274:36274-36280 (1999); Jensen et al., *J Immunol*, 158:3769-3778 (1997); Michaelson et al., *Eur J Immunol*, 22:1819-1825 (1992); Vlad et al., *J Exp Med*, 196:1435-1446 (2002); Werdelin et al., *Proc Natl Acad Sci USA*, 99:9611-9613 (2002). Most of these studies have investigated the processing and presentation of post-translationally glycosylated proteins. These epitopes appear to be simple mono- or di-saccharides linked to peptides. It has been shown that MHCI binds to the glycopeptides—and not just the peptide portion—of these types of epitopes. In addition, T-cell receptor (TCR) binding to the processed glycopeptides has been shown to be dependent on contact of the TCR with the epitope formed by both the glycan and the peptide that is bound to MHC. Haurum et al., *J Exp Med*, 180:739-744 (1994). For instance, Holmdahl and colleagues showed that epitope glycosylation plays a critical role in T-cell recognition of type II collagen (CII). Corthay et al., *Eur J Immunol*, 28:2580-2590 (1998); Dzhambazov et al., *Eur J Immunol*, 35:357-366 (2005); Michaelson et al., *Eur J Immunol*, 22:1819-1825 (1992). These investigators have found that the immunodominant T-cell epitope in healthy joint cartilage of humans and rats is O-glycosylated. Studies of glycopeptide epitopes derived from tumor antigen mucin-like glycoprotein1 (MUC1) are of particular importance. Hanish and Ninkovic, supra. In tumor cells, protein glycosylation forms tumor-specific glycopeptide epitopes that can be recognized by CD4$^+$ T cells. Vlad et al. (2002), supra; Werdelin et al., *Proc Natl Acad Sci USA*, 99:9611-9613 (2002). Changes in glycosylation patterns can alter epitope recognition by T cells. Hanish and Ninkovic, supra.

Over the past 15 years several successful vaccines in which polysaccharides are the key component have been introduced into clinical use. The most successful of these vaccines have been glycoconjugates in which the capsular polysaccharide (CPS) of a bacterial target is coupled to a protein carrier; this coupling induces T cell help to promote IgM-to-IgG switching, long-lived responses, and immunogenicity in children. The success of these vaccines varies with the population being immunized and with the characteristics of the specific vaccine. For example, pneumococcal conjugates have met with very good success in children, but have not lived up to expectations in adults (Siber et al., *Science* 265(5177):1385-1387 (1994).

The most widely accepted hypothesis underlying strategies for the preparation of glycoconjugate vaccines is that such vaccines are taken up through polysaccharide-specific B cells possibly after processing by dendritic cells and/or macrophages (Guttormsen et al., *Inf. Imm.* 67(12):6375-6384 (1999); Jones, *Anais da Academia Brasileira de Ciências* 77(2):293-324 (2005)). A peptide epitope of the carrier protein is subsequently presented to T cells. The resulting help provided to the polysaccharide-specific B cells by these activated T cells induces production of polysaccharide-specific IgG even though the T cells are activated by the MHC II bound peptides. However, little or no information exists on whether or not the T-cell epitopes are formed by the peptides generated from the glycoconjugate carriers or by epitopes formed by both the carbohydrate and peptides.

SUMMARY

The present invention is based, at least in part, on the discovery of methods of making glycoconjugate vaccines with enhanced immunogenicity and therefore greater therapeutic efficacy.

Thus, in one aspect, the invention provides methods for preparing a glycated peptide conjugate. The methods include: obtaining a population of polysaccharides; optionally treating the population of polysaccharides to create a population of oligosaccharides having an average molecular weight of about 5-20 kDa, e.g., about 10-15 kDa, e.g., about 10 kDa or 15 kDa; contacting the population of oligosaccharides with polypeptides comprising a plurality of repeating peptide units linked together by cleavable moieties, e.g., an acid-labile sequence or a protease recognition sequence, e.g., a cathepsin or caspase recognition sequence, wherein each peptide unit consists of:

(i) an MHC-II binding sequence, that is 50 amino acids or fewer, e.g., 40 amino acids or fewer, 30 amino acids or fewer, 20 amino acids or fewer, or 15 amino acids or fewer, e.g., about 8-15 amino acids;

(ii) one or more lysine residues; preferably, there is one lysine at an end, e.g., the C terminal end, and no internal lysines (in some embodiments, each peptide has a single lysine residue at the C terminal end); and optionally (iii) one or more amino acids linking the MHC-II binding sequence and the lysine reside;
under conditions sufficient to link oligosaccharides directly to lysine residues, e.g., by reductive amination, such that the ratio of oligosaccharides to peptide units is approximately 1:1, thereby preparing a glycated peptide conjugate.

In some embodiments, each of the peptide units comprises the same MHC-II binding sequence; in other embodiments, the peptide units comprise a plurality of MHC-II binding sequences.

In another aspect, the invention provides methods for preparing a glycated peptide/nanoparticle conjugate. The methods include obtaining a population of polysaccharides; optionally treating the population of polysaccharides to create a population of oligosaccharides having an average molecular weight of about 5-20 kDa, e.g., about 10-15 kDa, e.g., about 10 kDa or 15 kDa; contacting the population of oligosaccharides with a population of peptide units, wherein each peptide unit consists of:

(i) an MHC-II binding sequence, that is 50 amino acids or fewer, e.g., 40 amino acids or fewer, 30 amino acids or fewer, 20 amino acids or fewer, or 15 amino acids or fewer, e.g., about 8-15 amino acids;

(ii) one or more lysine residues; preferably there is one lysine at an end, e.g., the C terminal end, and no internal lysines (in some embodiments, each peptide has a single lysine residue at the C terminal end); and optionally (iii) one or more amino acids linking the MHC-II binding sequence and the lysine reside;
under conditions sufficient to link the oligosaccharides directly to lysine residues, e.g., by reductive amination, such that the ratio of oligosaccharides to peptide units is approximately 1:1, thereby preparing a glycated peptide conjugate; providing a biocompatible nanoparticle; and linking the N terminal end of the peptide to the biocompatible nanoparticle via a cleavable linker, e.g., an acid-labile sequence or a protease recognition sequence, e.g., a cathepsin or caspase recognition sequence.

In a further aspect, the invention provides glycated peptide conjugates and glycated peptide/nanoparticle conjugates prepared by a method described herein.

In an additional aspect, the invention features glycated peptide conjugates, including:
(1) a polypeptide portion comprising a plurality of repeating peptide units linked together by cleavable moieties, e.g., an acid-labile sequence or a protease recognition sequence, e.g., a cathepsin or caspase recognition sequence, wherein each peptide unit consists of:

(i) an MHC-II binding sequence, that is 50 amino acids or fewer, e.g., 40 amino acids or fewer, 30 amino acids or fewer, 20 amino acids or fewer, or 15 amino acids or fewer, e.g., about 8-15 amino acids;

(ii) one or more lysine residues; preferably there is one lysine at an end, e.g., the C terminal end, and no internal lysines (in some embodiments, each peptide has a single lysine residue at the C terminal end); and optionally (iii) one or more amino acids linking the MHC-II binding sequence and the lysine reside; and
(2) an oligosaccharide portion, preferably having an average molecular weight of about 5-20 kDa, e.g., about 10-15 kDa, e.g., about 10 kDa or 15 kDa, linked directly to the lysine residues, such that the ratio of oligosaccharides to peptide units is approximately 1:1.

In yet another aspect, the invention features glycated peptide/nanoparticle conjugates including a plurality of glycated peptides, each including:
(1) a peptide unit portion consisting of:
(i) an MHC-II binding sequence, that is 50 amino acids or fewer, e.g., 40 amino acids or fewer, 30 amino acids or fewer, 20 amino acids or fewer, or 15 amino acids or fewer, e.g., about 8-15 amino acids;

(ii) one or more lysine residues; preferably there is one lysine at an end, e.g., the C terminal end, and no internal lysines (in some embodiments, each peptide has a single lysine residue at the C terminal end); and optionally (iii) one or more amino acids linking the MHC-II binding sequence and the lysine reside; and
(2) an oligosaccharide, preferably having an average molecular weight of about 5-20 kDa, e.g., about 10-15 kDa, e.g., about 10 kDa or 15 kDa, linked directly to the lysine residues of the peptide units, such that the ratio of oligosaccharides to peptide units is approximately 1:1, wherein the glycated peptides are linked to a biocompatible nanoparticle at the C terminal end of the peptide unit, via a cleavable linker, e.g., an acid-labile sequence or a protease recognition sequence, e.g., a cathepsin or caspase recognition sequence.

In some embodiments, the polysaccharide is from a pathogen selected from the group consisting of viruses, bacteria, protozoa, and fungi. In other embodiments, the polysaccharide is from a tumor-associated glycoprotein.

In some embodiments, treating the polysaccharide comprises exposing the polysaccharide to ozonolysis or enzymatic digestion, e.g., with one or more glycosidases.

In some embodiments, each of the peptide units comprises the same MHC-II binding sequence. In some embodiments, the peptide units comprise a plurality of MHC-II binding sequences.

Also featured in another aspect of the invention are methods of inducing an immune response in a subject. The methods include administering a therapeutically effective amount of a glycated peptide conjugate or glycated peptide/nanoparticle conjugate as described herein.

In an additional aspect, the invention provides compositions comprising the glycated peptide conjugates and/or glycopeptide/nanoparticle conjugates described herein, in a pharmaceutically acceptable carrier.

Also within the invention is the use of the glycopeptide conjugates and/or glycated peptide/nanoparticle conjugates described herein, for inducing an immune response in a subject, and in the manufacture of a medicament for inducing an immune response in a subject. The medicament can be used in a method for treating or preventing infection in a patient suffering from or at risk for infection, or a person having a tumor. The medicament can be in any form described herein, and can be administered alone or in combination with, e.g., an adjuvant or immune stimulant.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 2A-E show the results of immunoprecipitations of Raji cell lysates. FIG. 2A is a line graph showing [$^3$H]GBSIII analyzed in lysates of Raji B cell endosomes (after 18 h of incubation); molecular size was determined by Superose 12 gel permeation chromatography. Cell-surface content was immunoprecipitated with HLA-DR mAbs. No [$^3$H]GBSIII was found in the co-IP product. FIG. 2B is a line graph showing [$^3$H]GBSIII-OVA analyzed from Raji B-cell endosomes (after incubation for 3 hours, 6 hours, and 18 hours); again, molecular size distribution was determined by Superose 12 chromatography. FIG. 2C is a line graph showing the elution profile on a Superose 12 column of [$^3$H]GBSIII-OVA obtained from the surface of mouse splenocytes (after incubation for 18 hours) and co-immunoprecipitated with antibody to HLAIA/IE. FIG. 2D is a histogram and bar graph showing the result of flow cytometric analysis of BMDCs after incubation (18 hours) with GBSIII, OVA, or GBSIII-OVA followed by surface staining of the cells with AlexaFluor633-conjugated mAb to GBSIII. FIG. 2E is an image showing complexes of HLA-DR and glycated peptide epitopes detected by Western blotting of SDS gels individually stained with antibodies to GBSIII, OVAp, and HLA-DR. *Quantitative densitometry analysis of each GBSIII-OVAp band was performed by normalization with its corresponding GBSIII band.

FIGS. 3A-B show the results of immunoprecipitations with [$^3$H]GBSIII-OVA and [$^3$H]GBSIII-TT in Raji cells. FIG. 3A is a bar graph showing the results from Raji B cells incubated (18 hours) with [$^3$H]GBSIII-OVA; cell surface content was co-immunoprecipitated with HLA-DR mAb, and LAMP-1 mAb as a control (co-IP with HLA-DQ or HLA-DP mAbs didn't show significantly enhanced radioactivity, p>0.05 when compared to LAMP-1 background). Data are expressed as mean±SD values. FIG. 3B is a line graph showing the results of co-immunoprecipitating [$^3$H]GBSIII-TT with MHCII mAbs from Raji B cells. Superose 12 molecular sizing column analysis (triangles) revealed that low-molecular-weight GBSIII (~10 kDa) was bound to MHCII molecules at the Raji cell surface. As a negative control, this experiment was repeated with MHCII-deficient Raji cells (RJ2.2.5), and no tritiated oligosaccharide was detected at the cell surface (squares). As a control for the mAb to MHCII used for co-IP, an antibody to LAMP-1 was used; no counts were detected in this immunoprecipitate.

FIGS. 4A-4C are line graphs depicting the processing of GBSIII[3H]-OVA (20 µg, 1800 cpm/ng) in the endosomes of Raji B cells (3×10$^6$/mL/well). GBSIII[$^3$H]-OVA was incubated in Raji cells for 18 hours either alone or in the presence of ROS scavengers: (4A) D-Mannitol, (4B) 4-OH TEMPO, (4C) sodium pyruvate. The end products from whole cell lysates were analyzed on Superose 12.

FIGS. 6A-E are bar graphs of CD4+ T cell proliferation in response to GBSIII-OVA immunization. CD4+ T cells recognize carbohydrate when the glycated peptide is presented on the APC surface by MHCII. BALB/c mice received two doses of GBSIII-OVA. Splenic CD4+ T cells from these mice were expanded in vitro for 9 days with GBSIII-OVA. An ELISPOT assay of the expanded T-cell population, along with irradiated naïve mouse splenocytes, was conducted with several antigens, including GBSIII coupled to a heterologous carrier (GBSIII-TT), for detection of T cells secreting IL-2 (FIG. 6A), IL-4 (FIG. 6B), and IFN γ (FIG. 6C). As a positive control, TT alone induced a strong response with all three cytokines in studies with lymphocytes from TT-immunized mice. ELISA was used to measure subclasses of IgG antibodies specific for OVA (FIG. 6D) and GBSIII (FIG. 6E) in serum from the GBSIII-OVA twice-immunized mice. *Antibody titers were recorded as the reciprocal dilution that resulted in an A405 of 0.5 when the reference antibody to GBSIII (50 ng/mL) reached an A405 of 0.5.

FIGS. 7A-D depict cell proliferation following immunization with GBSIII-OVAp. Wild-type (wt) BALB/c mice (7A) and DO11.10 mice (7B) were immunized three times (doses 2 weeks apart) with GBSIII-OVAp. Naive irradiated splenic APCs (105/well) were cocultured with CD4+ T cells (105/well) from each mouse strain for 4 days and then stimulated by either OVAp or GBSIII-OVAp (adjusted to contain the same amount of OVAp). Proliferation was measured by incorporation of [$^3$H]thymidine 8 hours before harvesting. Data are expressed as mean±SD values. Negative controls included stimulation by GBSIII (7.5 µg), scrambled OVAp (2.5 µg), or no antigen; all negative controls incorporated <500 cpm of [$^3$H]thymidine. As a positive control, *Staphylococcus* enterotoxin A induced the coculture to incorporate 54,700 cpm in wt T cells but <500 cpm in DO11.10 T cells. Not shown is the response of CD4+ T cells to OVAp at a similarly high level whether the cells came from naïve DO11.10 mice or from GBSIII-OVAp immunized mice. (7C and 7D) Brefeldin A blocks antigen presentation (by trapping MHCII within the endoplasmic reticulum), and mAb to IA/IE blocks mouse MHCII.

FIGS. 8A-C are bar graphs showing antibody titers following immunization with GBSIII-OVAp. DO11.10 and wild-type (wt) Balb/c mice were immunized three times with GBSIII-OVAp, and ELISA was used to measure titers of GBSIII-specific IgG (8A) and GBSIII-specific IgM (8B). OVAp-specific IgG titers in DO11.10 and wt mice immunized twice with OVAp alone are also shown (8C). *Antibody titers were reported as the reciprocal dilution that resulted in an A405 of 0.5 when the reference antibody to GBSIII (50 ng/mL) reached an A405 of 0.5. Both wt and DO11.10 mice had no detectable antibodies (titer, <1:50) to either GBSIII or OVAp before immunization.

FIGS. 14A-B are bar graphs depicting ELISA quantitative antibody titers to GBSIII in BALB/c mice receiving primary and secondary doses of different antigen combinations. (14A) GBSIII-specific IgG titers (μg/mL) in serum collected on day 21 from mice primed on day 0 and boosted on day 14 with different combinations of priming and boosting antigens. (14B) GBSIII-specific IgG titers (μg/mL) in serum collected on day 14 from mice primed with GBSIII, GBSIII-OVA, or GBSIII-TT. ***GBSIIIOVA-primed, GBSIII-boosted mice and GBSIII-primed, GBSIII-TT-boosted mice had significantly lower GBSIII-specific IgG titers than both GBSIII-OVA-primed, GBSIII-OVA boosted mice and GBSIII-OVA-primed, GBSIII-TT boosted mice (p<0.0001).

FIG. 15A is the structure of zwitterionic heparosan (e.g., *E. coli* K5 polysaccharide) oligosaccharide derivatives.

DETAILED DESCRIPTION

Figure 1:
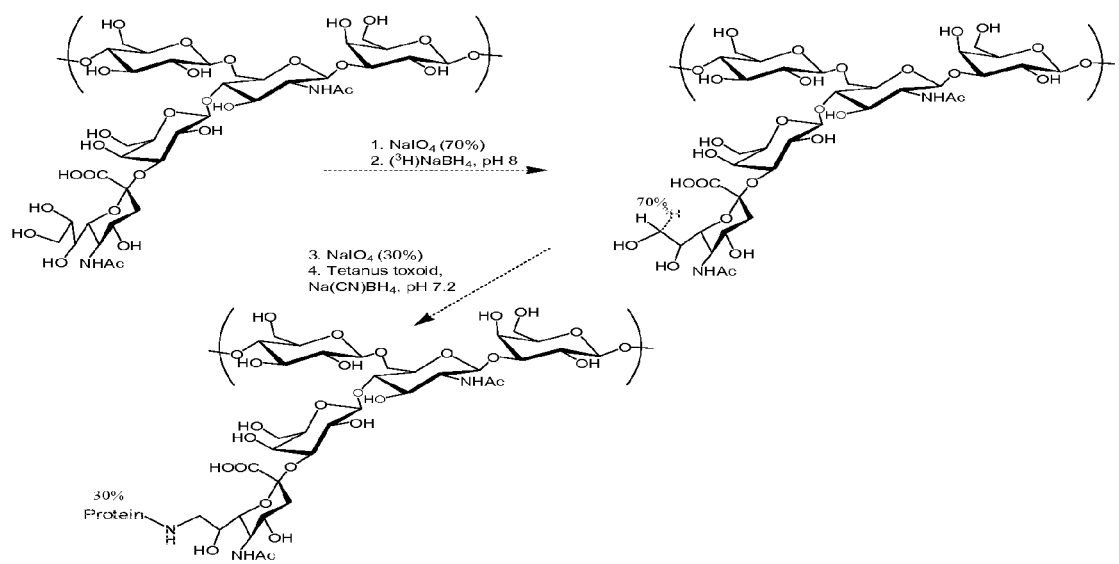
FIG. 1 is a schematic illustration of an exemplary method for radiolabeling of GBSIII followed by conjugation with carrier protein/peptide.

As noted above (see the Background), the prevailing paradigm for explaining glycoconjugate activation of T cells is that only the peptide is presented to and recognized by T cells, even though the carbohydrate is attached to the protein by an extremely strong covalent bond (a secondary amine in many cases). This classic hypothesis does not explain what happens to the polysaccharide within the APC or how the carbohydrate and protein come apart within the endosome (there being be no known mechanism within an endosome to break the secondary amine bonds), with subsequent presentation of just the peptide to the T cell. As described herein, glycated peptides are actually presented to T cells by professional APCs. Furthermore, the carbohydrates presented by MHCII in the present glycoconjugate vaccine (about 10 kDa) are much smaller than naturally occurring polysaccharides (generally larger than 100 kDa, up to millions of kDa).

The knowledge gained from the studies described herein, about the mechanism of processing and presentation of glycoconjugate vaccines, can be applied to designing and synthesis of new generation vaccines. The information has allowed the present inventors to design target specific, structurally based vaccine candidates. As one theory, not meant to be limiting, this design may enable faster presentation of glycated peptides by the MHCII pathway, eliminating the endosomal processing step (either partially or completely). In addition, this design may result in a higher ratio of immunogenic glycated peptides per weight of vaccine administered, potentially resulting in a more robust response for the same dose, or allowing the use of reduced doses.

Such new vaccines include the following:
1) A carbohydrate, e.g., an about 5-20 kDa, e.g., 10-15 kDa, carbohydrate (smaller or larger if necessary to effectively crosslink B cell receptors and activate the B cell) covalently linked to a polypeptide construct that is comprised of repeating T cell epitopes, e.g., OVAp, linked by cleavable linkers. This will enable the depolymerisation of the polypeptide in the acidic endosome creating many glycated peptide residues.
2) A carbohydrate, e.g., an about 5-20 kDa, e.g., 10-15 kDa, carbohydrate (smaller or larger if necessary to effectively crosslink B cell receptors and activate the B cell) covalently linked to a polypeptide constructs comprised of multiple different T cell peptide epitopes linked by cleavable linkers. This should enable recruitment of a larger T cell repertoire.
3) A biopolymer based nanoparticle coated with the glycated peptide antigenic epitopes of a glycoconjugate vaccine, e.g., comprising an about 5-20 kDa, e.g., 10-15 kDa, carbohydrate (the size of the MHCII bound polysaccharide) covalently linked to one end of a T cell epitope, e.g., OVAextpep, by cleavable linkers.

Each of these embodiments includes the following elements:
I: a carbohydrate moiety: a polysaccharide or oligosaccharide from a pathogen or tumor of interest, optionally treated to have an average molecular weight of about 5-20 kDa, e.g., 10-15 kDa, or smaller or larger as needed to effectively crosslink B cell receptors and activate the B cell; and
II: at least one peptide unit that includes an MHCII binding sequence and a lysine, preferably a single lysine at one end, to which the carbohydrate is directly bound.

The peptide unit acts as an anchor that binds to MHCII molecules on antigen presenting cells (APCs) such as dendritic cells and B cells; through this anchor the carbohydrate is bound to the MHCII and presented to a T cell. Because the MHCII binding sequences are presented as small peptide units that require little or no degradation, and the carbohydrates are pre-digested to a smaller size that is readily presentable by the APC, processing time through the endosome can be greatly reduced, resulting in faster immune responses. Methods of identifying, selecting, an preparing these elements are well known in the art; the following provides a list of exemplary elements.

Carbohydrate Antigens

The compositions described herein can be made using any polysaccharides to which an immune response is desired, e.g., obtained from any pathogen, e.g., viruses, bacteria, fungi, or protozoa; glycoprotein; or cell, e.g., tumor cells. A "polysaccharide" is meant any linear or branched polymer consisting of monosaccharide residues, usually linked by glycosidic linkages, and thus includes oligosaccharides. Methods of identifying and obtaining carbohydrates of interest are known in the art, see, e.g., Dormitzer et al., Trends Biotechnol. 26(12):659-667 (2008).

Carbohydrate-containing structures abound at the bacterial surface (Nikaido, *Rev Infect Dis,* 10:S279-S281 (1988)) and include capsules, lipopolysaccharides, teichoic acids, peptidoglycans, and glycoproteins. CPSs consist of several hundred repeating units; each unit may contain from one to eight sugars that are usually (though not always) linked glycosidically. Variations in sugar composition, ring forms, linkage positions, anomeric-center configurations, isomer forms, conformation, and charge-motif all contribute to differences in the immunologic epitopes that are present. Any of these structures can be used in the methods and compositions described herein.

In some embodiments, the glycoconjugate compositions described herein are made using a carbohydrate derived from a bacterium, e.g., a capsular polysaccharide (CPS). Exemplary bacteria include: *Streptococcus pneumoniae, Pneumococci, Meningococci, Neisseria meningitides, Haemophilus influenzae* (e.g., *Haemophilus influenzae* b), *Salmonella typhi, Shigella dysenteriae, Bacteroides fragilis,* Group A and Group B *Streptococci, Salmonella, Escherichia coli, Vibrio cholerae, Citrobacter, Hafnia, Proteus, Staphylococcus,* and *Klebsiella pneumoniae.* See, e.g., Vliegenthart et al., *FEBS Letters* 580:2945-2950 (2006), and references cited therein; Jones, *Anais da Academia Brasileira de Ciências* 77(2):293-324 (2005) (especially Tables I and II) and references cited therein; Cohen et al., *J. Immunol.* 180:2409-2418 (2008); and Weintraub, *Carbohydrate Research* 338:2539-2547 (2003).

In some embodiments, the glycoconjugate compositions described herein are made using a carbohydrate derived from a parasite, e.g., cell surface carbohydrates, e.g., (glycosylphosphatidylinositol anchors (GPIs)). In general, the bacterium will be a clinically relevant bacterium, i.e., a pathogenic (disease-causing) bacterium. Exemplary parasites include *Plasmodium falciparum* (malaria); *Toxoplasma gondii* (toxoplasmosis); and *Leishmania major* (leishmaniasis). See, e.g., Vliegenthart et al., *FEBS Letters* 580:2945-2950 (2006), and references cited therein;

In some embodiments, the glycoconjugate compositions described herein are made using a carbohydrate derived from a virus, e.g., from a viral envelope glycoprotein, e.g., N-glycans. In general, the virus will be a clinically relevant virus, i.e., a pathogenic (disease-causing) virus. Exemplary viruses include human immunodeficiency virus (HIV) (e.g., HIV-1 glycoprotein gp120), Respiratory Syncytial Virus (RSV), Hepatitis B Virus (HBV), varicella zoster, herpes simplex virus type 2, rabies, measles, and ebola. See, e.g., Wang, *Current Opinion in Drug Discovery & Development* 9(2):194-206 (2006); Johnson et al., *Journal of General Virology* 83:2663-2669 (2002); Langenberg, *Ann. Int. Med.* 122(12):889-898 (1995); Vafai, *Vaccine* 13(14):1336-1338 (1995); Ruigrok and Gerlier, *PNAS* 104 (52):20639-20640 (2007).

In some embodiments, the glycoconjugate compositions described herein are made using a carbohydrate derived from a tumor cell, e.g., cell surface carbohydrates, e.g., from glycoproteins. Exemplary glycoproteins include Mucin-1 (MUC-1) (breast cancer), NER-2/neu (breast cancer), carcino-embryonic antigen (CEA) (e.g., colorectal, lung, breast and pancreatic cancers), p53, Sialyl Tn (STn) (breast cancer); and Globo H (breast and prostate cancers). Ganglioside molecules (e.g. GM2, GD2, GD3) are also expressed on several cancer cells. See, e.g., Vliegenthart et al., *FEBS Letters* 580:2945-2950 (2006), and references cited therein; Xu et al., *J Exp Med.* 199(5):707-716 (2004).

The carbohydrate portion of the glycoconjugates described herein optionally can be prepared by degrading native or whole polysaccharides into a population having an average molecular weight of about 10-20 kDa, e.g., 10-15 kDa, e.g., 10 kDa. Methods are known in the art for preparing the polysaccharides, e.g., using acid, base, oxidative (e.g., using reactive oxygen or nitrogen species), or enzymatic-catalyzed hydrolysis. For example, ozonolysis can be used, e.g., as described in Paoletti et al., *J. Biol. Chem.* 265(30) 18278-18283 (1990); Kalka-Moll et al., *J. Immunol.* 164: 719-724 (2000); and U.S. Pat. Nos. 6,027,733 and 6,274,144. In some embodiments, a combination of methods is used to produce a polysaccharide composition having the desired average molecular weight.

The process of degrading the polysaccharides can be monitored using methods known in the art, e.g., FPLC as described in U.S. Pat. Nos. 6,027,733 and 6,274,144, and stopped when the desired average molecular weight is reached.

In alternative embodiments, native or whole polysaccharides can be used.

T Cell Epitopes that Bind to MHCII

In general, the MHCII binding sequences are peptides that include T cell epitopes, e.g., CD4+ T helper cell epitopes (Etlinger et al., *Science* 249:423-425 (1990)). Many CD4+ epitopes that can induce T cell help are known in the art, see, e.g., Etlinger et al., 1990, supra; Valmori et al., *J. Immunol.* 149:717-721 (1992); Sadd et al., *Immunology* 76:599-603 (1992); Kumar et al., *J. Immunol.* 148:1499-1505 (1992); Kaliyaperumal et al., *Eur J Immunol* 25:3375-3380 (1995); DeVelasco et al., *Infect. Immun.* 63:961-968 (1995); Falugi et al., *Eur. J. Immunol.* 31:3816-3824 (2001); and Bixer et al., *Adv. Exp. Med. Biol V*:175-180 (1989)).

CD4+ epitopes that are useful in the present methods and compositions include those from diphtheria toxoid (DT), tetanus toxin (TT), *Plasmodium falciparum circumsporozite*, hepatitis B surface antigen, hepatitis B nuclear core protein, *H. influenzae* matrix protein, *H. influenzae* haemagglutinin, group B *N. meningitidis* outer membrane protein complex (OMPC), the pneumococcal toxin pneumolysin, and heat shock proteins, e.g., from *Mycobacterium bovis* and *M. leprae*, and recombinantly produced, genetically detoxified variants thereof, or a recombinantly-produced, non-toxic-mutant of *Pseudomonas aeruginosa* exotoxin A or *Staphylococcus* exotoxin or toxoid. See, e.g., Amir-Kroll et al., *Vaccine* 24:6555-6563 (2006); Amir-Kroll et al., *Journal of Immunology* 170:6165-6171 (2003); and Könen-Waisman et al., *J. Inf. Dis.* 179:403-13 (1999).

In some embodiments, the MHCII binding sequence is from cross reactive material of diphtheria toxoid (CRM197) (Shelly et al., *Inf. Immun.* 65:242-247 (1997)), key hole limpet hemocyanin (KLH), or the outer membrane complex of *Neisseria meningitides* (Vella et al., *Inf. Immun.* 60:4977-4983 (1992)). See, e.g., Vliegenthart et al., *FEBS Letters* 580:2945-2950 (2006), and references cited therein.

The T cell epitope peptides can be produced synthetically or recombinantly, e.g., by expression in a bacterial or other cell culture system as known in the art. For example, a recombinant peptide can be generated by expression from an encoding nucleic acid in a host cell. Any host cell can be used depending upon the individual requirements of a particular vaccine system. One of skill in the art would readily be able to select and use a suitable host cell. In some embodiments, bacterial hosts are used for the production of recombinant protein, due to the ease with which bacteria may be manipulated and grown. An exemplary bacterial host is *Escherichia coli*. See, e.g., U.S. Pat. No. 6,855,321. A combined solid-phase and solution method can also be used, e.g., a modification of the methods described in Riniker et al., *Tetrahedron* (49)41:9307-9320 (1993).

The T cell epitope will preferably not include any lysine residues internally, but will be modified to include at least one lysine residue at an end, e.g., at the C terminus. In some embodiments, there is only one lysine residue at the C terminus or at the N terminus. The placement of the lysine reside is constrained only by the need to preserve the ability of the peptide to bind to MHCII when linked to a carbohydrate.

In some embodiments, there will also be one or more amino acids between the MHC binding sequence and the lysine residue, i.e., a spacer sequence. Such spacer sequences can be any amino acid except lysine, and will generally be flexible and have small R groups, to avoid steric hindrance and allow for optimal positioning of the linked carbohydrate for presentation to T cells and access of the peptide epitope to bind to MHCII. Exemplary amino acids suitable for inclusion in the linker include glycine, alanine, and serine.

In embodiments wherein the MHC binding sequences are linked in tandem in a single polypeptide (as opposed to on the surface of a nanoparticle), the peptide units are linked by cleavable moieties, e.g., amino acid sequences that are recognized and cleaved by proteases or other enzymes, or chemical moieties that are acid labile. A number of such cleavable moieties are known in the art. For example, cleavable sequences can include those recognized by cathepsins, e.g., as described in Conus and Simon, *Biochemical Pharmacology* 76:1374-1382 (2008); Arnold et al., *Eur. J. Biochm.* 249: 171-179 (1997); Roberts, *Drug News Perspect* 18(10):605 (2005); and Plüger et al., *Eur. J. Immunol.* 32:467-476 (2002). In some embodiments, the cleavable sequence is a recognition sequence for a protease present in the endosome.

Acid labile moieties are also known in the art, and can include 4-(4-Hydroxymethyl-3-methoxyphenoxy)butyric acid (SIGMA), as described in Riniker et al., *Tetrahedron* (49)41:9307-9320 (1993).

Non-Peptide MHC Binding Moieties

In some embodiments, the MHC binding moiety is a small molecule, polymer, or peptide analog, rather than a amino acid sequence. In this embodiment, a conjugate vaccine can be include a polysaccharide or an oligosaccharide from a bacteria, virus, parasite or tumor linked with a carrier molecule that is not a protein or a peptide. Of skill in the art could select and use of any molecule of a size appropriate to fit into the MHCII binding site and bind to that site by electrostatic, hydrophobic, Van der Waals or other known chemical forces that allow 2 molecules to bind to each other. One example is a zwitterionic molecule, e.g., a zwitterionic carbohydrate such as polysaccharide A (PSA). These could be synthetic molecules with physico-chemical characteristics such as zwitterionic charges or hydrophobic characteristics allowing them to bind to MHCII. The polysaccharide or oligosaccharide that is to be the target of the induced immune response is coupled to this carrier molecule. The carrier serves in place of the peptide as the anchor to bind to MHCII and the target polysaccharide or oligosaccharide would be available for recognition by the T cell receptor in a manner similar to that for the glycated peptides described in this application. These new glycated carrier molecules would induce T cell responses required for helper function and antibody production.

As an alternative to natural zwitterionic polysaccharides such as PSA, chemically modified structurally well-defined oligosaccharides could be used as carrier molecules.

Glycated Peptide-Nanoparticles

Nanoparticles linked to the glycated peptides described herein via a cleavable linker can also be made and used according to the present invention. Thus, the invention further includes compositions comprising glycated peptides linked to biocompatible nanoparticles, optionally with co-localized antibodies that target the nanoparticles to APCs, e.g., DCs or B cells. In embodiments wherein the peptide units comprising MHC binding sequences are linked to a nanoparticle, there will be a cleavable moiety between each peptide and the nanoparticle. Exemplary nanoparticles include those described in Xu et al., *Macromol. Biosci.* 7:968-974 (2007).

The nanoparticles useful in the methods and compositions described herein are made of materials that are (i) biocompatible, i.e., do not cause a significant adverse reaction in a living animal when used in pharmaceutically relevant amounts; (ii) feature functional groups to which the binding moiety can be covalently attached, (iii) exhibit low non-specific binding of interactive moieties to the nanoparticle, and (iv) are stable in solution, i.e., the nanoparticles do not precipitate. The nanoparticles can be monodisperse (a single crystal of a material, e.g., a metal, per nanoparticle) or polydisperse (a plurality of crystals, e.g., 2, 3, or 4, per nanoparticle).

A number of biocompatible nanoparticles are known in the art, e.g., organic or inorganic nanoparticles. Liposomes, dendrimers, carbon nanomaterials and polymeric micelles are examples of organic nanoparticles. Quantum dots can also be used. Inorganic nanoparticles include metallic nanoparticle, e.g., Au, Ni, Pt and TiO2 nanoparticles. Magnetic nanoparticles can also be used, e.g., spherical nanocrystals of 10-20 nm with a $Fe^{2+}$ and/or $Fe^{3+}$ core surrounded by dextran or PEG molecules. In some embodiments, colloidal gold nanoparticles are used, e.g., as described in Qian et al., *Nat. Biotechnol.* 26(1):83-90 (2008); U.S. Pat. Nos. 7,060,121; 7,232, 474; and U.S. P.G. Pub. No. 2008/0166706. Suitable nanoparticles, and methods for constructing and using multifunctional nanoparticles, are discussed in e.g., Sanvicens and Marco, *Trends Biotech.*, 26(8): 425-433 (2008).

In some embodiments, the nanoparticles are attached (linked) to the glycated peptides described herein via functional groups. In some embodiments, the nanoparticles are associated with a polymer that includes the functional groups, and also serves to keep the metal oxides dispersed from each other. The polymer can be a synthetic polymer, such as, but not limited to, polyethylene glycol or silane, natural polymers, or derivatives of either synthetic or natural polymers or a combination of these. Useful polymers are hydrophilic. In some embodiments, the polymer "coating" is not a continuous film around the magnetic metal oxide, but is a "mesh" or "cloud" of extended polymer chains attached to and surrounding the metal oxide. The polymer can comprise polysaccharides and derivatives, including dextran, pullanan, carboxydextran, carboxmethyl dextran, and/or reduced carboxymethyl dextran. The metal oxide can be a collection of one or more crystals that contact each other, or that are individually entrapped or surrounded by the polymer.

In other embodiments, the nanoparticles are associated with non-polymeric functional group compositions. Methods are known to synthesize stabilized, functionalized nanoparticles without associated polymers, which are also within the scope of this invention. Such methods are described, for example, in Halbreich et al., *Biochimie*, 80(5-6):379-90, 1998.

In some embodiments, the nanoparticles have an overall size of less than about 1-100 nm, e.g., about 25-75 nm, e.g., about 40-60 nm, or about 50-60 nm in diameter. The polymer component in some embodiments can be in the form of a coating, e.g., about 5 to 20 nm thick or more. The overall size of the nanoparticles is about 15 to 200 nm, e.g., about 20 to 100 nm, about 40 to 60 nm; or about 60 nm.

Synthesis of Nanoparticles

There are varieties of ways that the nanoparticles can be prepared, but in all methods, the result must be a nanoparticle with functional groups that can be used to link the nanoparticle to the binding moiety.

For example, glycated peptides can be linked to metal oxide nanoparticles through covalent attachment to a functionalized polymer or to non-polymeric surface-functionalized metal oxides. In the latter method, the nanoparticles can be synthesized according to a version of the method of Albrecht et al., *Biochimie*, 80(5-6): 379-90 (1998). Dimercaptosuccinic acid is coupled to the nanoparticle and provides a carboxyl functional group. By functionalized is meant the presence of amino or carboxyl or other reactive groups that can be used to attach desired moieties to the nanoparticles, e.g., the glycated peptides described herein or antibodies.

In another embodiment, the glycated peptides are attached to the nanoparticles via a functionalized polymer associated with the nanoparticle. In some embodiments, the polymer is hydrophilic. In a specific embodiment, the conjugates are made using oligonucleotides that have terminal amino, sulfhydryl, or phosphate groups, and superparamagnetic iron oxide nanoparticles bearing amino or carboxy groups on a hydrophilic polymer. There are several methods for synthesizing carboxy and amino derivatized-nanoparticles. Methods for synthesizing functionalized, coated nanoparticles are discussed in further detail below.

Carboxy functionalized nanoparticles can be made, for example, according to the method of Gorman (see WO 00/61191). Carboxy-functionalized nanoparticles can also be made from polysaccharide coated nanoparticles by reaction with bromo or chloroacetic acid in strong base to attach carboxyl groups. In addition, carboxy-functionalized particles can be made from amino-functionalized nanoparticles by converting amino to carboxy groups by the use of reagents such as succinic anhydride or maleic anhydride.

Nanoparticle size can be controlled by adjusting reaction conditions, for example, by varying temperature as described in U.S. Pat. No. 5,262,176. Uniform particle size materials can also be made by fractionating the particles using centrifugation, ultrafiltration, or gel filtration, as described, for example in U.S. Pat. No. 5,492,814.

Nanoparticles can also be treated with periodate to form aldehyde groups. The aldehyde-containing nanoparticles can then be reacted with a diamine (e.g., ethylene diamine or hexanediamine), which will form a Schiff base, followed by reduction with sodium borohydride or sodium cyanoborohydride.

Dextran-coated nanoparticles can also be made and cross-linked, e.g., with epichlorohydrin. The addition of ammonia will react with epoxy groups to generate amine groups, see Hogemann et al., *Bioconjug. Chem.* 2000. 11(6):941-6, and Josephson et al., *Bioconjug. Chem.*, 1999, 10(2):186-91.

Carboxy-functionalized nanoparticles can be converted to amino-functionalized magnetic particles by the use of water-soluble carbodiimides and diamines such as ethylene diamine or hexane diamine.

Avidin or streptavidin can be attached to nanoparticles for use with a biotinylated binding moiety, such as an oligonucleotide or polypeptide. See e.g., Shen et al., *Bioconjug. Chem.*, 1996, 7(3):311-6. Similarly, biotin can be attached to a nanoparticle for use with an avidin-labeled binding moiety.

In all of these methods, low molecular weight compounds can be separated from the nanoparticles by ultra-filtration, dialysis, magnetic separation, or other means. The unreacted glycated peptides can be separated from the ligand-nanoparticle conjugates, e.g., by size exclusion chromatography.

In some embodiments, colloidal gold nanoparticles are made using methods known in the art, e.g., as described in Qian et al., *Nat. Biotechnol.* 26(1):83-90 (2008); U.S. Pat. Nos. 7,060,121; 7,232,474; and U.S. P.G. Pub. No. 2008/0166706.

In some embodiments, the nanoparticles are pegylated, e.g., as described in U.S. Pat. Nos. 7,291,598; 5,145,684; 6,270,806; 7,348,030, and others.

In some embodiments, the glycated peptides are attached to the nanoparticles as a complete unit; in some embodiments, the peptide units are attached to the nanoparticles before the carbohydrates are added.

Methods of Constructing the Glycoconjugates

In the glycoconjugates described herein, the peptide is preferably covalently linked directly to the carbohydrate, e.g., using reductive amination. Other methods are known in the art; see, e.g., Vliegenthart et al., *FEBS Letters* 580:2945-2950 (2006), and references cited therein. Preferably, no chemical linkers will be used, i.e., no hexanoic acid, adipic acid, or other bifunctional coupling molecules. See, e.g., Jones, *Anais da Academia Brasileira de Ciências* 77(2):293-324 (2005).

The glycoconjugates can be constructed using methods known in the art, e.g., methods used to produce other glycoconjugate vaccines, see, e.g., Purcell et al., *Nat. Rev. Drug Disc.* 6:404-414 (2007); Falugi et al., *Eur. J. Immunol.* 31:3816-3824 (2001); Dziadek et al., *Chem. Eur. J.* 14:5908-5917 (2008).

Exemplary Glycoconjugates

Group B Strep (GBS) Glycoconjugates: GBS is the foremost cause of life-threatening bacterial infections in newborns. Schuchat, *Lancet*, 353:51-56 (1999). In ~80% of cases, neonatal GBS infection is acquired during delivery by direct mother-to-baby transmission of the pathogen, which colonizes the anogenital mucosa of 25-40% of healthy women (reviewed in Schuchat (1999), supra). Despite the recommendation of the Centers for Disease Control and Prevention that appropriate antibiotics be administered to all GBS-positive women before delivery (an intervention that dramatically reduces the incidence of GBS disease), GBS still causes ~2500 cases of infection and 100 deaths annually among newborns in the United States alone. In any event, the policy of offering such antibiotic treatment is likely to be unsustainable in the long run because of the threat of antibiotic resistance. Therefore, effective vaccination is commonly considered the only means by which to reduce the incidence of GBS disease over the long term.

The rationale for GBS vaccine development is supported by the observation that the risk of neonatal infection is inversely proportional to the maternal level of specific antibodies to the capsular polysaccharide (CPS) antigen that surrounds GBS (De Jong et al., *Int Immunol*, 16(2):205-213 (2004); Paoletti et al., *Infect Immun*, 69:6696-6701 (2001)); the implication is that protective IgG is transferred from the mother to the baby through the placenta. The approach to developing a vaccine against GBS described herein has been the generation of conjugate vaccines prepared with purified CPS antigens. Conjugate vaccines against all nine GBS serotypes have been developed and shown in preclinical studies to induce CPS-specific IgG that is functionally active against GBS of the homologous serotype. Paoletti and Madoff, *Semin Neonatol,* 7:315-323 (2002).

Clinical phase 1 and phase 2 trials of conjugate vaccines prepared with CPSs from GBS types Ia, Ib, II, III, and V revealed that these preparations are safe and highly immunogenic in healthy adults (reviewed in Paoletti and Madoff (2002), supra). The long history of GBS vaccine research makes these vaccines an ideal prototype to use for the studies of glycoconjugate antigen processing, presentation and characterization of the responses by stimulated T cells. The GBSIII glycoconjugates described are "model" antigens, and are relevant to real and important disease.

Pharmaceutical Formulations

A therapeutically effective amount of one or more of the compositions described herein (i.e., that include as an active (therapeutic) agent a glycoconjugate as described herein, either alone or bound to a nanoparticle) can be incorporated into pharmaceutical compositions suitable for administration to a subject, e.g., a human. Such compositions typically include the composition and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances are known. Except insofar as any conventional media or agent is incompatible with the active compound, such media can be used in the compositions of the invention. Supplementary active compounds can also be incorporated into the compositions, e.g., an inhibitor of degradation of the ligand.

A pharmaceutical composition can be formulated to be compatible with its intended route of administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR EL™ (polyethoxylated castor oil; BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the composition (e.g., an agent described herein) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, PRIMOGEL™ (sodium carboxymethyl starch), or corn starch; a lubricant such as magnesium stearate or STEROTES™; a glidant such as colloidal silicon dioxide; a sweetening agent such as sucrose or saccharin; or a flavoring agent such as peppermint, methyl salicylate, or orange flavoring.

Systemic administration can also be by transmucosal or transdermal means. For transmucosal or transdermal administration, penetrants appropriate to the barrier to be permeated are used in the formulation. Such penetrants are generally known, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Nucleic acid molecules can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al., *PNAS* 91:3054-3057, 1994). The pharmaceutical preparation of the gene therapy vector can include the gene therapy vector in an acceptable diluent, or can include a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack, or dispenser together with instructions for administration. In one aspect, the pharmaceutical compositions can be included as a part of a kit.

Generally the dosage used to administer a pharmaceutical compositions facilitates an intended purpose for prophylaxis and/or treatment without undesirable side effects, such as toxicity, irritation or allergic response. Although individual needs may vary, the determination of optimal ranges for effective amounts of formulations is within the skill of the art. Human doses can readily be extrapolated from animal studies (Katocs et al., Chapter 27 In: "Remington's Pharmaceutical Sciences", 18th Ed., Gennaro, ed., Mack Publishing Co., Easton, Pa., 1990). Generally, the dosage required to provide an effective amount of a formulation, which can be adjusted by one skilled in the art, will vary depending on several factors, including the age, health, physical condition, weight, type and extent of the disease or disorder of the recipient, frequency of treatment, the nature of concurrent therapy, if required, and the nature and scope of the desired effect(s) (Nies et al., Chapter 3, In: Goodman & Gilman's "The Pharmacological Basis of Therapeutics", 9th Ed., Hardman et al., eds., McGraw-Hill, New York, N.Y., 1996).

Methods of Inducing an Immune Response

Also provided herein are methods of inducing an immune response in a subject, e.g., a mammal, e.g., a human or non-human mammal. The glycoconjugates described herein are particularly effective at inducing an immune response to the native polysaccharides themselves, e.g., for use as vaccines. Thus, the methods can include identifying a subject in need of immune protection, and administering a glycoconjugate as described herein to the subject in an amount sufficient to induce an immune response in the subject. In some embodiments, the methods include administering one or more additional doses, e.g., booster doses, to the subject.

The methods described herein can be used in any subjects, but are particularly useful in subjects who are immune compromised or immunodeficient, and subjects who are typically poor responders to vaccination, as well as those who are at high risk of infection. Such subjects include those who are very young (e.g., infants less than 24 months old), subjects with end stage renal disease (ESRD) (particularly those on hemodialysis), cancer patients undergoing chemotherapy and radiation therapy, subject with HIV/AIDS, alcoholics, drug abusers, diabetic subjects, the elderly (particularly those in extended care facilities), subjects with invasive surgical procedures (e.g., organ transplantation), and other subjects in acute care settings.

In some embodiments, the compositions described herein are co-administered with an adjuvant or immunostimulant. In some embodiments, the compositions described herein are administered without any adjuvant or immunostimulant.

EXAMPLES

The invention is further described in the following examples, which do not limit the scope of the invention described in the claims.

Example 1

The Carbohydrate Portion of a Model Glycoconjugate is Expressed in the Context of MHCII on the APC Surface The presently accepted paradigm for how glycoconjugates activate T cells is that only the peptide is presented to and recognized by T cells, even though the carbohydrate is attached to the protein by an extremely strong covalent bond (a secondary amine in many cases). This classic hypothesis does not explain what happens to the polysaccharide within the APC or how the carbohydrate and protein come apart within the endosome, with subsequent presentation of just the peptide to the T cell. However, certain CPSs—e.g., polysaccharide A (PSA) of the common intestinal gram-negative obligate anaerobe *Bacteroides fragilis*—activate the innate immune system through Toll-like receptors (TLRs) and that the innate immune system works in conjunction with the adaptive immune system in responding to these molecules. Wang et al., *J Exp Med*, 203:2853-2863 (2006). PSA is processed by antigen-presenting cells (APCs) and presented through the major histocompatibility class II (MHCII) pathway to $CD4^+$ T cells, which are consequently activated. Cobb et al., *Cell*, 117:677-687 (2004). The present inventors hypothesized that glycated peptides, if properly processed, can be presented to T cells by professional APCs. This novel concept runs counter to the classic teaching about conjugate vaccines and infection with glycoprotein-containing viruses and bacteria. To determine whether this hypothesis was worth pursuing, experiments were performed using GBSIII, whose repeating-unit structure is shown in FIG. 1, as a model polysaccharide. GBSIII is considered a classic T cell-independent antigen. Guttormsen et al., *Infect Immun*, 67:6375-6384 (1999). In mice, significant levels of IgG antibodies are induced by immunization with GBSIII only if it is covalently bonded to a carrier protein. (FIG. 1 shows exemplary chemistry for use in conjugation).

Example 2

Glycated Peptides are Presented on the Surface of APCs

To determine whether MHCII-associated glycated peptides are presented on the surface of APCs, co-immunoprecipitation (co-IP), flow cytometry, and western blot experiments were conducted. First, it was assessed whether pure GBSIII was depolymerized within the endosome of APCs, as were PSA and N-acetylated PSA. Using methods identical to those published for PSA (see Cobb et al. (2004), supra), (Duan et al., Proc. Natl. Acad. Sci. U.S.A. 105(13):5183-5188 (2008)) radiolabeled GBSIII was incubated with Raji B cells for 18 hours. Then microsomes were isolated from the Raji cells, and it was determined that the molecular size of GBSIII within the endosome was significantly smaller (dispersed in size, with an average of ~15 kDa, but containing some material at the bed volume of the column) than that of the native molecule (average, 150 kDa; eluted at the void volume of the column) (FIG. 2a). Next a co-IP experiment (FIG. 2a), technically similar to that published for PSA (see Cobb et al. (2004), supra), was conducted. Surface immune complexes were precipitated with a mAb to MHCII. When cells were incubated with pure unconjugated polysaccharide, as expected, no GBS carbohydrate was found on the cell surface in the context of MHCII. These data shows that unconjugated GBSIII is depolymerized within the endosome but pure carbohydrates cannot be loaded onto the MHCII molecule and is therefore not presented on the cell surface. The chemical key to PSA-MHCII binding is the zwitterionic charge motif, which unconjugated GBSIII (like most other carbohydrates) lacks. $^3$H dextran was similarly found to be processed in the endosome. These findings suggest that at least one mechanism rendering polysaccharides T cell independent is an inability to bind to MHCII., not necessarily an inability of an APC to depolymerize the polysaccharide to a size consistent with loading onto MHCII.

Co-IP experiments using mAb to MHCII after incubation of a glycoconjugate ([$^3$H]GBSIII-OVA) with either mouse splenic mononuclear cells (FIG. 2C) or Raji B cells (FIG. 3A) demonstrated that [$^3$H]GBSIII was surface associated. In co-IP experiments with [$^3$H]GBSIII-OVA as antigen, surface-associated GBSIII was sought with anti-HLA-IA/IE on splenocytes from C57Bl/6 wildtype mice and various knockout strains (FIG. 2C). Although splenocytes from both wild-type and MHCI$^{-/-}$ mice had carbohydrate presented on their surface (~10 kDa), cells from MHCII$^{-/-}$ (H2-Ab1) mice lacked GBSIII on their surface. Co-IP using Raji B cells as APCs demonstrated that the carbohydrate epitope was presented on the cell surface in the context of the HLA-DR molecule (FIG. 3A). To ensure that the MHC molecule was presenting the carbohydrate and that carbohydrate presentation in a glycoconjugate vaccine was not specific to OVA as a carrier, a conjugate of GBSIII coupled to tetanus toxoid ([$^3$H]GBSIII-TT) was prepared. Co-IP studies with Raji B cells and the latter vaccine construct also demonstrated that GBSIII was presented on the surface of Raji B cells in the context of HLA-DR (FIG. 3B) but not on the surface of an MHCII deficient Raji-derived cell line, RJ2.2.5. In all co-IP experiments, a mAb to LAMP-1, which is not found on the cell surface but only in the endosomal compartment, was used as a negative control.

For validation of the co-IP experiments, flow cytometry was used to examine the presentation of carbohydrate epitopes by APCs. Mouse bone marrow-derived dendritic cells (BMDCs) were incubated with GBSIII, OVA, or GBSIII-OVA for 18 hours. The cells were labeled at 4° C. with a fluorophore-conjugated mAb specific for GBSIII and then fixed. Only the membranes of GBSIII-OVA-incubated BMDCs—and not those of cells incubated with pure unconjugated GBSIII or OVA—were labeled with GBSIII antibody (FIG. 2D).

The above experiments show that carbohydrate epitopes are presented by the MHCII pathway only when polysaccharides are conjugated to carrier proteins. One explanation for this observation is that the GBSIII carbohydrate epitopes can bind to the MHCII molecule only when they are bound to a peptide epitope (e.g., in a glycated peptide). Perhaps a peptide epitope that is covalently linked to a carbohydrate epitope is generated, binds to MHCII, and carries the carbohydrate to the surface of the APC on the MHCII molecule. This possibility was examined by investigating whether what is presented by the MHCII protein is GBSIII chemically coupled to a peptide. Western blot experiments were conducted on cell-surface extracts of Raji B cells that had been incubated with a glycoconjugate containing a single peptide epitope as the carrier molecule. An ovalbumin peptide epitope, OVA323-339, was conjugated to GBSIII to form GBSIII-OVAp. OVA323-339 represents both a T- and a B-cell epitope of OVA (23). This peptide was N-acetylated at its N terminus and extended with four amino acids at the C terminus to permit nonrandom conjugation to the polysaccharide. These modifications did not affect the pure peptide's binding to MHCII and the αβ TCR. By mass, the peptide-to-carbohydrate ratio of the glycoconjugate was 3:1; this value corresponded to an average of 8 repeating units of carbohydrate bound to one peptide molecule to make up ~10-kDa glycated-peptide epitopes along the polysaccharide chain. The 10-kDa size was similar to that of the depolymerized carbohydrate found on the cell surface of polysaccharide/protein conjugates incubated with Raji B cells and mouse splenocytes. GBSIII-OVAp and pure GBSIII were each incubated with Raji B cells, and the cell-surface contents were collected, solubilized, run on Tris-Glycine/polyacrylamide gels, and transferred to polyvinylidene difluoride membranes for western blot analyses. Membranes were incubated with HLA-DR antibody or with antibodies to either GBSIII or OVAp. Immune complexes containing HLA-DR, carbohydrate, and peptide were all seen in a band at ~80 kDa on the gels of cell-surface extracts obtained from GBSIIIOVAp-incubated cells but not from GBSIII-incubated cells (FIG. 2E). HLA-DR αβ dimers (self peptide-loaded or empty) were labeled with HLA-DR mAb at ~65 kDa as described previously (24) (data not shown). The ~15-kDa difference in size (determined by protein markers) between unloaded HLA-DR and the glycated peptide-HLA-DR complex represents the size of the glycated peptide (~10 kDa), as carbohydrates mobilize more slowly than proteins in gels.

Example 3

Endosomal Processing of GBSIII-OVA

A preliminary study on the kinetics of endosomal processing of GBSIII-OVA was also performed. Endosomes of Raji cells were collected after 3 hours, 6 hours, or 18 hours of incubation with GBSIII [$^3$H]-OVA (FIG. 2B). The result suggests that processing starts in 3 hours and reaches completion by 18 hours.

Preliminary data have been obtained on the mechanism of processing of the carbohydrate portion of conjugate vaccines (e.g., III-OVA) into products to be presented to T cells by APCs. A likely mechanism of polysaccharide processing by reactive oxygen species (ROSs) was elucidated. There are also possible roles of reactive nitrogen species and glycosidases in processing of GBSIII in the endosomes.

Figure 4B:
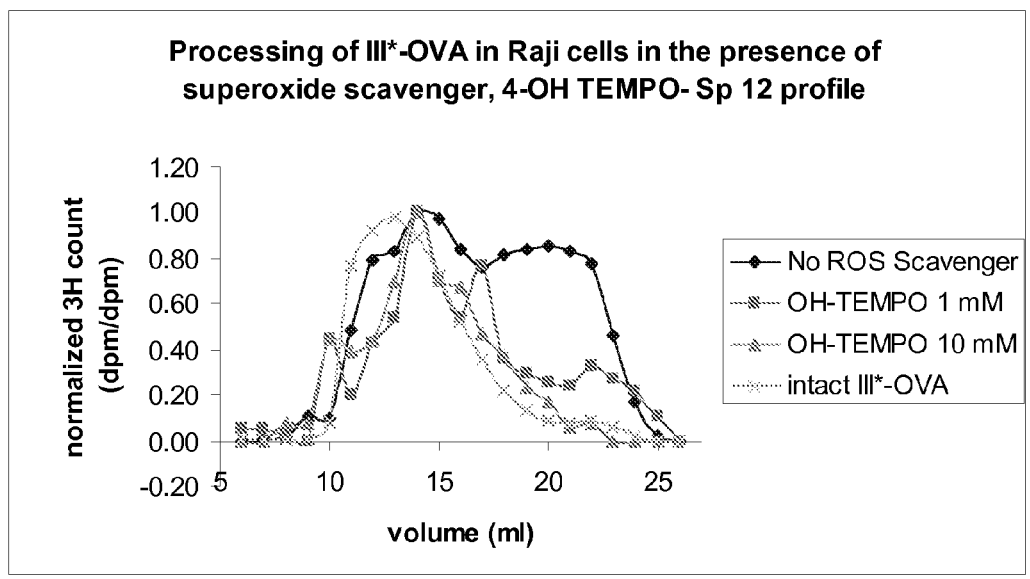
Figure 4C:
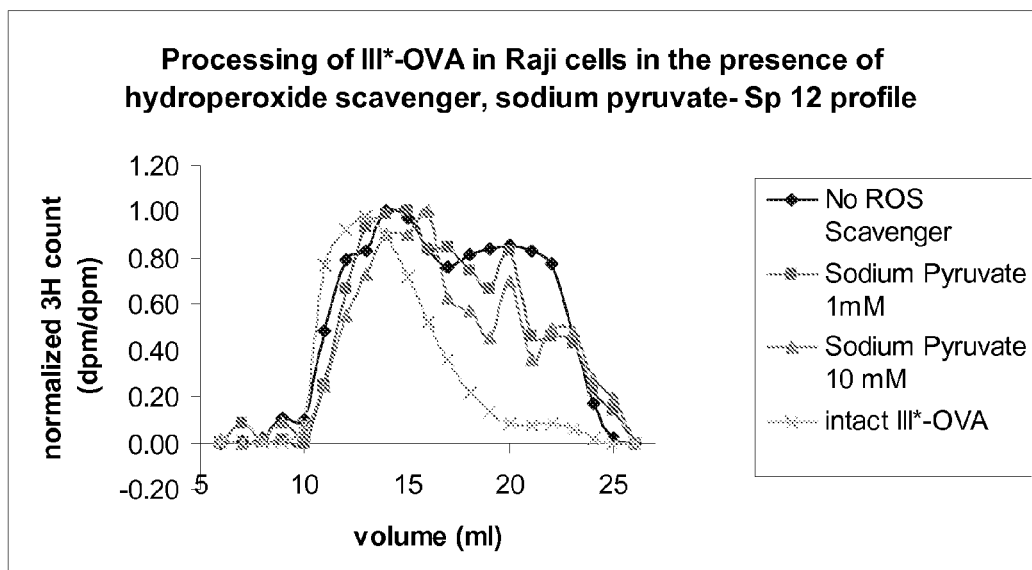

After uptake by Raji B cells, III-OVA is degraded to a smaller molecular size (FIG. 4A-C). Degradation is suppressed by the hydroxyl radical scavenger D-mannitol (FIG. 4A) or the superoxide scavenger 4-hydroxyl TEMPO (FIG. 4B) but not by the hydroperoxide scavenger pyruvate (FIG. 4C).

These data indicate that carbohydrate portion of GBSIII-OVA is depolymerized within the APC endosome/lysosome by ROSs, most possible by superoxide and hydroxyl radical.

The results with the Raji B cell line supported the hypothesis that glycoconjugate vaccines contain glycated peptide epitopes. In summary, the data suggest that a ~10 kDa portion of GBSIII is presented on the surface of APC in association with an MHCII molecule when conjugated with a carrier protein.

Three key control experiments were performed that ruled out any possibility of that carbohydrate presentation was an experimental artifact. First, unconjugated polysaccharide was compared with the conjugated one and showed that the unconjugated polysaccharide was depolymerized in the endosomes but not presented on the surface, while the conjugated sugar was both depolymerized in the endosomes and presented on the cell surface. Second, the processing and presentation of tritiated glycoconjugate was compared in Raji cells and RJ2.2.5 cells, a Raji B cell line lacking MHCII proteins. The lack of presentation in the RJ2.2.5 cells clarified that what we observed in the Raji Cells were due to MHCII molecules. Finally, in all of the experiments when performing the final immunoprecipitation step along with monoclonal antibody to MHCII molecule, anti-HLA-DR, the surface extract was also precipitated with control antibodies (e.g. anti-LAMP-1 antibody), this served as a negative control.

B cells are the key APCs that present the processed antigenic epitope of glycoconjugate vaccine to CD4+ T cells. Thus the use of Raji B cell line in these processing and presentation experiments is relevant. To validate these experiments in primary cells, mouse splenic lymphocytes and bone marrow derived dendritic cells (BMDCs) were used as APCs to repeat the above experiments.

Example 4

OVApeptide (OVAp) Specific T Cells Don't Recognize III-OVAp Epitope

This example describes an experiment demonstrating that CD4+ T cell receptors (TCRs) recognizing a particular peptide (OVAp) didn't recognize the same peptide when that peptide is conjugated with a capsular polysaccharide (GB-SIII). This experiment was performed to collect evidence supporting the hypothesis that the carbohydrate portion of the glycated peptide epitope can be specifically recognized by certain TCRs. Showing that GBSIII-OVAp doesn't induce T cell proliferation of an OVAp specific T cell clone as well as OVAp alone would suggest that III-OVAp possesses glycated peptide epitopes that can't be recognized by peptide specific T cells.

Figure 5A:
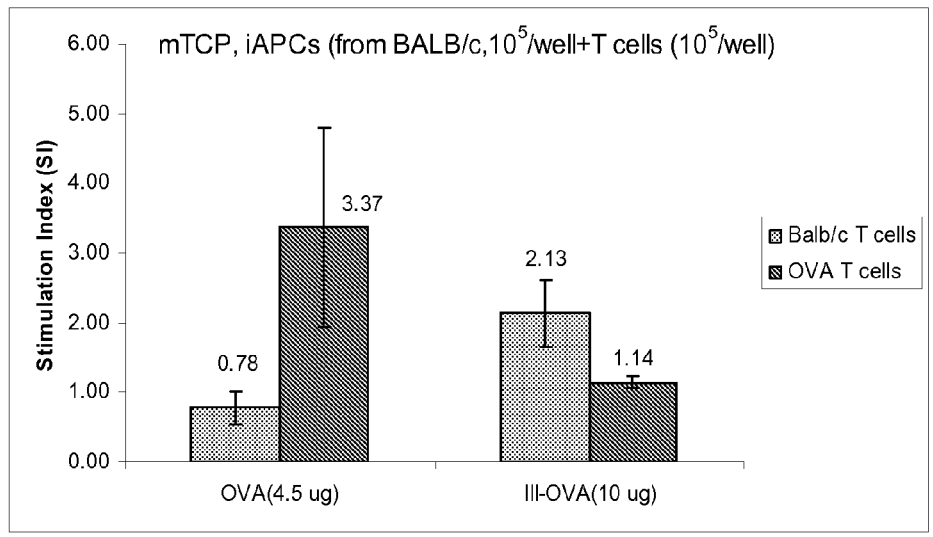
FIGS. 5A-5B are bar graphs depicting T cell proliferation experiment: Irradiated APCs (10$^5$/well) and CD4+ T cells (10$^5$/well) were incubated at 37° C., 5% $CO_2$ for four days (obtimized proliferation time) in the presence of antigen and treated with $^3$H thymidine 8 hours before harvesting. Radioactive uptake was measured by liquid scintillation. The $^3$H count (cpm) for each APC-T cell population was divided by the $^3$H count of the mixture of APCs and T cells with no antigen (negative control, usually gives $^3$H count of 200-500 cpm) and this number gives the stimulation index (SI). Since APCs are irradiated and can't proliferate the 3H count represents proliferation of T cells. SI for unstimulated T cells were normalized to 1. For instance, SI of 3 could be regarded as there are 3 times more T cells in that mixture than in the unstimulated (no antigen added) mixture.
Figure 5B:
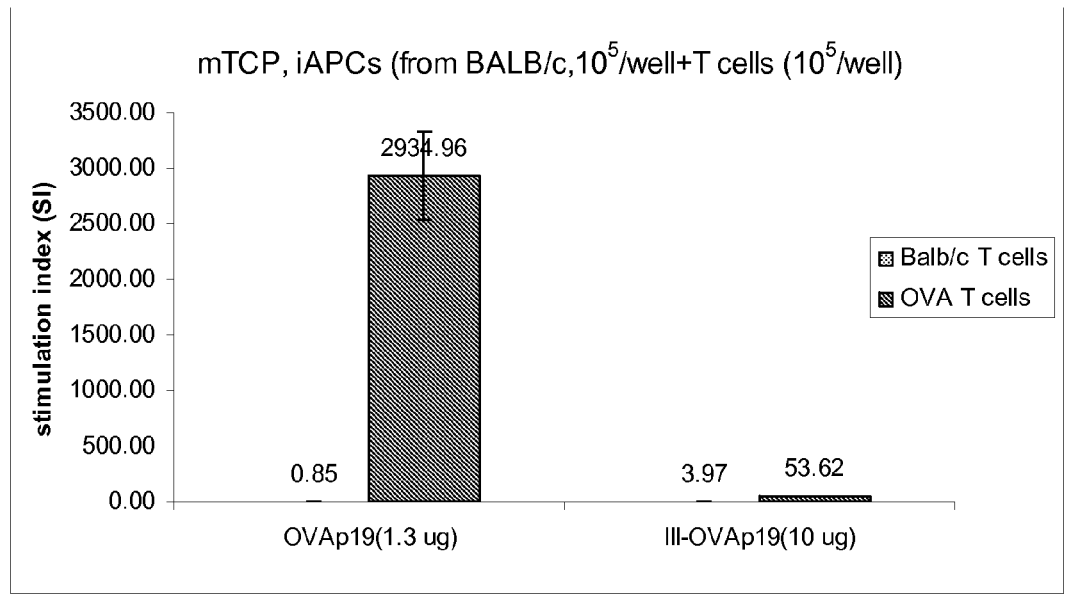

Ovalbumin antigenic epitope OVA323-339 represents a T and B cell epitope of OVA, which is important in the generation and development of immediate hypersensitivity responses in BALB/c mice. McFarland et al., *Biochemistry,* 38:16663-16670 (1999). A peptide was designed and prepared by adding lysine groups to both termini of OVAp (OVAp19, referring to 19 amino acids with two lysine groups added to 17 aa OVAp). This peptide was conjugated with GBSIII (GBSIII-OVAp) and performed T cell proliferation experiments co-incubating irradiated APCs from wt BALB/c mice with CD4+ T cells from either BALB/c or OVAp T cell mice, DO11.10; A T-cell receptor transgenic line expressing a T-cell receptor that recognizes OVA peptide 323-339 (OVAp) derived from ovalbumin in the context of an MHC class II (I-A$^d$) molecule (FIGS. 5A-B). The APC+T cell mixtures were stimulated with GBSIII (8.7 µg, equivalent amount to GBSIII content of 10 µg GBSIII-OVAp), GBSIII-OVA (10 µg), OVA (4.5 µg, equivalent amount to OVA content of 10 µg GBSIII-OVA), GBSIII-OVAp (10 µg), OVAp (1.3 µg equivalent amount to OVAp content of 10 µg GBSIII-OVAp), OVAp19 (1.3 µg).

As controls, the same experiment was repeated adding anti-HLA IA/IE (and its isotype as a control to anti HLA IA/IE) to show that T cell stimulations are due to MHCII presentation. A scrambled OVA peptide, scOVAp, having the same amino acid content as OVAp but in a totally different order was prepared. This peptide was used to show that TCR specificity was to OVAp only. This scrambled peptide didn't induce T cell proliferation. *Staphylococcal* enterotoxin A (SEA, 10 ng) and concanavalin A (conA, 10 ng) superantigens were used as positive controls (approximately 50-1000 stimulation index).

All the controls in this experiment worked perfectly. Neither III-OVA(p) nor OVA(p) were able to stimulate T cell proliferation when MHCII molecules are blocked with anti HLA IA/IE, and the proliferation activity was at the original value in the presence of the isotype for anti HLA IA/IE. This clearly shows MHCII dependency of T cell proliferations. In FIGS. 5A-B, for simplicity, only the key results of this experiment are displayed.

GBSIII didn't stimulate T cells from either wt BALB/c or OVA T cell mice. GBSIII-OVA and OVA stimulated two different cell populations selectively. While GBSIII-OVA was able to induce proliferation of BALB/c T cells (SI: 2.1), it didn't stimulate OVAp specific T cells (SI: 1.1). On the other hand OVA stimulated OVAp T cells (SI: 3.4) but couldn't stimulate BALB/c T cells (SI: 0.8). This observation suggests that both antigens are activating T cells through different T cell epitopes. The epitope of GBSIII-OVA can't be recognized by OVA T cells but there is a T cell receptor repertoire in the BALB/c T cells that recognize GBSIII-OVA epitope.

An interesting observation was made on the stimulation of OVAp and GBSIII-OVAp. OVAp induces proliferation of OVAp specific T cells enormously (SI: 2935.0), while having no effect on the stimulation of BALB/c Tcells (SI: 0.85). GBSIII-OVAp on the other hand stimulates both groups of T cells (BALB/c T cells SI: 4.0, OVAp T cells SI:53.6). The same pattern observed here was seen with OVA and III-OVA stimulation. BALB/c T cells while lacking a TCR for OVAp, are able to recognize the antigenic epitope of III-OVAp, suggesting that III-OVAp has an epitope with a sugar molecule on it since there can only be one peptide epitope for both III-OVAp and OVAp. Another very important potential conclusion drawn from this experiment was that OVAp T cells don't recognize the III-OVAp epitope since there was approximately sixty fold decrease in T cell proliferation of OVA T cell stimulation with GBSIII-OVAp (SI: 53.6) when compared to stimulation with OVAp of the same amount (SI: 2935.0). Indeed serial dilutions of OVAp were still better stimulating (0.13 µg OVAp-SI: 781, 0.013 µg OVAp-SI: 35) than 10 µg GBSIII-OVAp (having 1.3 µg OVAp content). These results suggest that III-OVAp has a glycated peptide epitope and when that epitope is presented, TCR of OVAp T cells don't recognize this glycated peptide resulting in a dramatic reduction in the stimulation of these T cells when compared to OVAp stimulation.

Example 5

Response of CD4+ T Cells to Glycated Peptides

T cells recognize certain MHCII-bound carbohydrates (ZPSs), and this recognition results in biologically important outcomes. The unique and critical chemical characteristic of ZPS required for MHCII binding is the zwitterionic charge motif, which allows electrostatic ZPSMHCII binding. Unconjugated GBSIII and nearly all other carbohydrates lack a zwitterionic charge motif and instead have either negatively charged groups only or no charged groups at all as part of their repeating-unit structure. These findings suggest that at least one mechanism rendering polysaccharides T cell independent is an inability to bind to MHCII, and not necessarily an inability of the αβ TCR of a CD4+ T cell to recognize carbohydrates.

T-cell proliferation assays were performed to determine whether T cells could recognize the carbohydrate portion of the MHCII-bound glycated peptide generated in the endosomes and presented on the surface of APCs. Wild-type BALB/c mice were immunized with GBSIII-OVA to expand the repertoire of T cells recognizing epitopes generated by GBSIII-OVA. CD4+ T cells were collected from the spleens of these mice and further expanded in the presence of APCs for 9 days by in vitro stimulation with GBSIII-OVA. This procedure was designed to foster the proliferation not only of T cells that recognize OVA (peptides) but also of T cells recognizing GBSIII epitopes (i.e., by recognition of peptide-bound carbohydrate) and GBSIII-OVA epitopes (i.e., by recognition of both the peptide and carbohydrate), should such T cells exist. This protocol also eliminated unstimulated T cells (i.e., those that were not specific for these antigens) during the 9-day coculture period. After coculture, IL-2-, IL-4-, and IFN-γ-producing CD4+ T cells were assayed by ELISPOT assay in supernatants of restimulated cocultures of expanded T cells and APCs (FIGS. 6A, 6B, and 6C). Several antigens were used in the ELISPOT assay. Initially, the cytokine profiles for OVA and GBSIII-OVA restimulation of T cells were compared. As shown in FIGS. 6B and 6C, OVA induced significantly higher IFN-γ secretion and significantly lower IL-4 secretion than did GBSIII-OVA—a result suggesting that while OVA stimulates both Th2 and Th1 cells, GBSIII-OVA preferentially stimulates Th2 cells. The greater production of IL-4 by GBSIII-OVA than by OVA alone may represent useful information in the induction of optimal immune responses to glycoconjugate vaccines.

The subclasses of OVA-specific IgG (IgG1, IgG2a, IgG2b) represented in serum from GBSIII-OVA-immunized mice suggested that both IFN-γ and IL-4 were stimulating B cells, while the GBSIII-specific IgG subclass (IgG1 only) represented B-cell stimulation by IL-4 (FIGS. 6D and 6E). This finding suggests that a unique population of CD4+ T cells responds to the carbohydrate portion of the glycated peptide that drives IgG switching.

Confirmation of the presence of a carbohydrate-responding T-cell population was again sought with an ELISPOT assay. The CD4+ T cells used after the initial 9-day expansion with GBSIII-OVA (discussed above) were restimulated in this assay with a GBSIII glycoconjugate in which the GBSIII polysaccharide was conjugated to a different carrier protein, tetanus toxoid (TT), to produce GBSIII-TT. Since the T cells used were expanded initially with GBSIII-OVA, they recognized only those epitopes generated from GBSIII or OVA. If this population included a subpopulation of T cells that recognized only GBSIII, they would be stimulated by GBSIII-TT but not by TT. In fact, the data shown in FIGS. 6A, 6B, and 6C validate this assumption and clearly show a population of T cells recognizing the GBSIII polysaccharide.

Example 6

Response of OVAp-Specific TCRs to Glycated Peptides

Next, a glycoconjugate was constructed in which the T-cell response was directed toward only one carrier peptide. The possibility existed that certain conjugates with full-length protein were presenting more immunogenic peptides after conjugation and thus that an enhanced immune response was directed toward a peptide that was more immunogenic than the peptide presented by the protein carrier if given alone. GBSIII-OVAp, which contains only a single peptide T-cell epitope, was used as the antigen. Lymphocytes were obtained from both OVAp specific TCR transgenic (DO11.10) mice and wild-type (BALB/c) mice after each mouse strain was immunized with three doses of GBSIII-OVAp given 2 weeks apart. In T-cell proliferation experiments, irradiated APCs from wild-type (BALB/c) mice were co-incubated with CD4+ T cells from either immune BALB/c mice (FIG. 7A) or immune DO11.10 mice (FIG. 7B). The iAPC/CD4+ T-cell mixtures were stimulated in vitro with one of three antigens: GBSIII-OVAp (10 μg); GBSIII (7.5 μg, with a GBSIII content equivalent to that in the 10-μg dose of GBSIIIOVAp); and OVAp (2.5 μg, with an OVAp content equivalent to that in the 10-μg dose of GBSIII-OVAp).

GBSIII did not stimulate T cells from either wild-type BALB/c or OVAp T cell transgenic mice. CD4+ T cells from wild-type mice immunized with GBSIII-OVAp responded better when the conjugate was administered than when the specific peptide used in the vaccine was administered alone (p=0.009); the implication is that the carbohydrate portion of GBSIIIOVAp—rather than the peptide—was being presented to the TCR. Construction of the conjugate with the same single antigenic peptide in both GBSIII-OVAp and OVAp demonstrates that the different T-cell responses to these two antigens cannot be accounted for by presentation of different peptide epitopes. With DO11.10 CD4+ T cells, OVAp induced a very strong proliferative response (285,000 cpm; FIG. 7B). An important finding was that DO11.10 CD4+ T cells did not appear to recognize OVAp when the coculture was stimulated with GBSIII-OVAp. Proliferation was ~23-fold lower in DO11.10 T cells stimulated with GBSIII-OVAp (12,687 cpm) than in those stimulated with the same amount of OVAp (285,000 cpm). These results suggest that III-OVAp has a glycated peptide epitope that, when presented, is not recognized by the TCR of DO11.10 transgenic OVA-specific T cells. As a result, the stimulation of these T cells by GBSIII-OVAp is dramatically reduced from that by OVAp. These findings also suggest that the carbohydrate is masking the presentation of OVAp on the APC surface. When brefeldin A was added to the APC/CD4+ cocultures to block MHCII presentation (by trapping MHCII molecules inside the endoplasmic reticulum) or when anti-HLA-IA/IE was added to inhibit MHCII recognition by T cells, no T-cell stimulation was observed—an outcome confirming that processing and presentation by MHCII is required (FIGS. 7C and 7D). In addition, a scrambled OVA peptide, scOVAp, with the same amino acid content as OVAp but in a totally different sequence, was used. Cocultures of APCs and CD4+ T cells from GBSIII-OVAp-immunized wt or DO11.10 mice did not respond to the scrambled peptide (<500 cpm); thus the TCR was specific to a peptide with the OVAp sequence alone.

Example 7

Mediating Polysaccharide-Specific Antibody Isotype Switching by B Cells

To determine whether the polysaccharide-specific antibody (IgG) response is due to recognition of a peptide epitope or a carbohydrate epitope, measured GBSIII-specific IgG titers were measured from DO11.10 OVAp-specific TCR transgenic mice and in wild-type BALB/c mice immunized with GBSIII-OVAp. DO11.10 transgenic mice did not produce GBSIII-specific IgG, while wild-type mice developed high titers of GBSIII-specific IgG (FIG. 8A). Moreover, DO11.10 mice and wildtype mice developed comparable amounts of GBSIII-specific IgM, a result indicating that the lack of IgG production in DO11.10 mice was not due to low numbers of GBSIII-specific B cells (FIG. 8A). These results support the hypothesis that the recognition of GBSIII by the TCR of helper T cells induces polysaccharide-specific IgG secretion by B cells. Since DO11.10 mice lack the T-cell repertoire recognizing the carbohydrate epitope of the glycoconjugate vaccines, DO11.10 T cells were not able to induce polysaccharide-specific IgG secretion by B cells. When wild-type and DO11.10 mice were immunized with OVAp (no polysaccharide), DO11.10 mice produced higher titers of OVAp-specific IgG (FIG. 8C). This latter experiment indicated that a deficiency in the ability of DO11.10 mice to produce IgG antibodies does not account for their failure to produce GBSIII-specific antibodies.

Example 8

T Cells May Respond to Carbohydrates Presented in the Context of a Glycoconjugate on the APC Surface The data suggest that bacterial CPSs like PSA and GBSIII can be processed to smaller molecular sizes in the endosome. These carbohydrates appear to traffic in a degraded form to the APC surface, where they appear to be detected bound to MHCII. It has been clearly shown in published studies that T cells respond to certain polysaccharides (ZPSs), with biologically important outcomes. Mazmanian et al., *Cell*, 122:107-118 (2005); Ruiz-Perez et al., *PNAS*, 102:16753-16758 (2005); Wang et al., *J Exp Med*, 203:2853-2863 (2006). It was next determined whether T cells respond to carbohydrates bound to MHCII through peptides (glycated peptides) presented by MHCII. Again, the hypothesis was that, when processing glycoconjugates or glycoproteins, APCs present glycated peptides to the T cell similar to how they present peptide epitopes derived from proteins.

Figure 9:
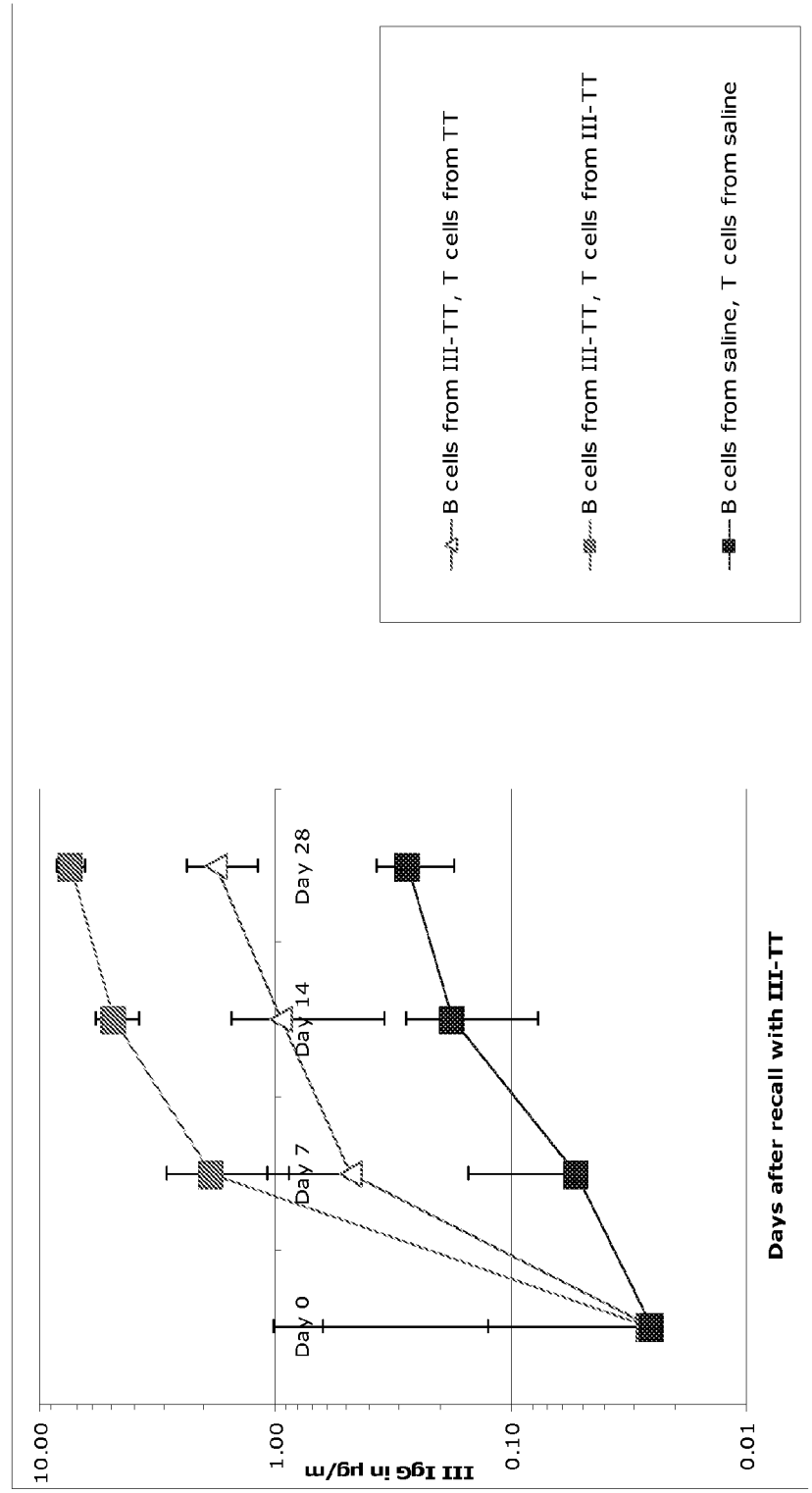
FIG. 9 is a line graph depicting an IgG response to recall immunization in mice receiving B cells from GBSIII-TT-primed mice and T cells from either TT-primed mice or GBSIII-TT-primed mice (p<0.01 for these two groups). Mice receiving naïve B and T cells from saline-treated donors served as controls. The differences between all groups were assessed by Kruskal-Wallis nonparametric analysis.

An adoptive transfer experiment was conducted. Groups of cell-donor Balb/c mice were primed with the GBSIII-TT vaccine or with TT alone. B cells ($10^8$) from spleens of GBSIII-TT-primed mice were transferred to two groups of naïve Balb/c recipients (six mice per group), which also received CD4$^+$ T cells ($0.5 \times 10^8$) from either GBSIII-TT-primed or TT-primed animals. CD4$^+$ T and B cells from saline-recipient naïve mice were used as controls. At 24 hours after cell transfer, the cell recipients were immunized with GBSIII-TT vaccine. The immune response in mice receiving T cells from GBSIII-TT-immunized animals was significantly enhanced over that in mice receiving T cells from animals immunized with TT alone ($p<0.01$; FIG. 9).

Since all recipient mice were given B cells from the same pool (GBSIII-TT-immunized), the differences in the magnitude of the response in recall-immunized animals were attributable to the T-cells source (GBSIII-TT-primed vs. TT-primed donors). It is possible that more favorable peptides (with better T-cell epitopes) were presented in recipients of T cells from GBSIII-TT-primed animals than in recipients of T cells from TT-immunized animals. However, it is equally plausible that donor T cells were better primed for GBSIII-TT than for TT recall—i.e., that the T cells from the GBSIII-TT-primed donors had been primed with and therefore recognized glycated peptides—and that, since the recall-immunized animals received the glycoconjugate, those that got T cells from III-TT-immunized animals now had T cells that recognized glycated peptides better than peptides alone.

These data support the hypothesis that T cells differentially recognize peptide and glycated peptides.

Example 9

Optimizing Peptide Glycoconjugates

Figure 10:
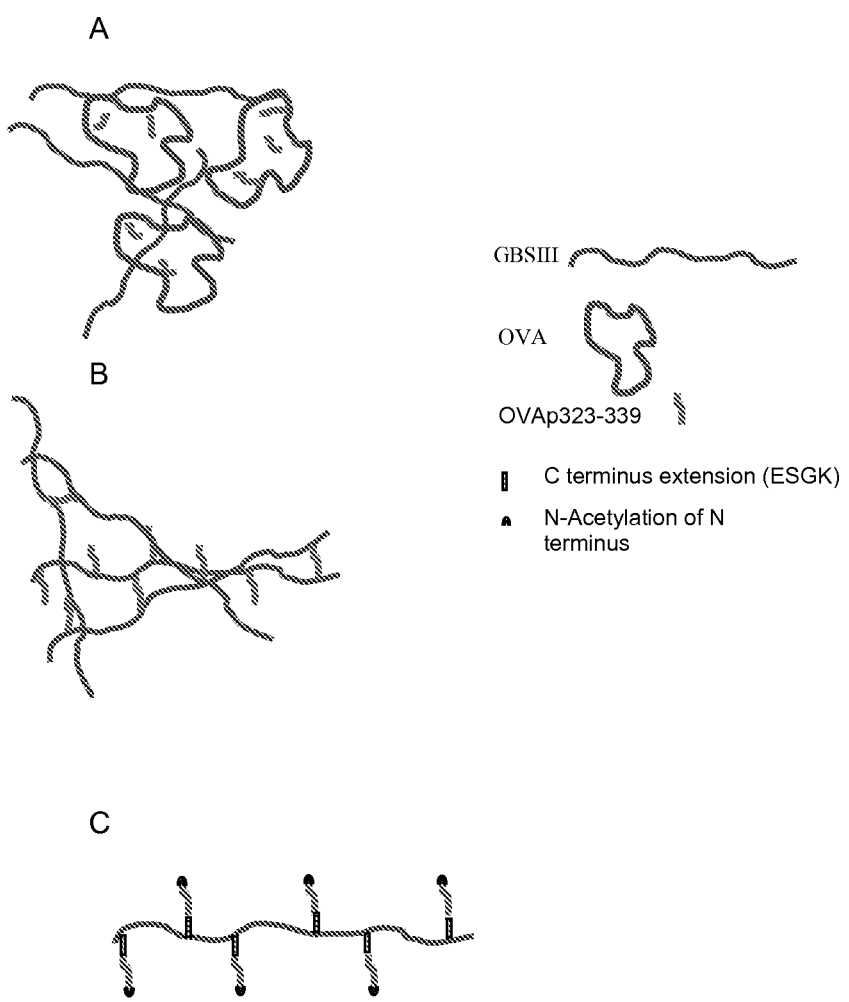
FIGS. 10A-C are cartoon representations of three vaccines GBSIII-OVA (9A), GBSIII-OVAp (10B), GBSIII-OVAext-pep (10C). While GBSIII-OVA and GBSIII-OVAp have bulky matrix-like structures, GBSIII-OVAextpep has highly uniform single-chain structure.

When mice were immunized with III-OVAp19 (OVAp19 refers to 19 amino acids, including two lysine groups added to each terminus of the 17 aa TCR dependent antigenic epitope of OVA, OVAp), no secretion of GBSIII specific IgGs was observed. A possible reason for why GBSIII-OVAp couldn't induce IgM-IgG switch might be something to do with the design of III-OVAp. The peptide in this construct covalently binds to the polysaccharide from both N and C termini. This double-sided binding likely results in entrapment of peptide in the highly crosslinked conjugate minimizing recognition of the peptide by the MHCII molecule in the endosome (FIG. 10B). The GBSIII-Ova-extended-peptide conjugate (III-OVAextpep) was designed and synthesized (FIG. 10C). Here OVAp(323-339) is extended on the C terminus with four amino acids, lysine being the C terminus residue. The amino functionality at the N-terminus is blocked by acetylation of the N-terminus amine. An extended OVAp was designed and synthesized: (N-acetyl)-ISQAVHAAHAEINEAGRESGK (SEQ ID NO:1). This peptide can only conjugate with GBSIII through C terminus lysine group leading to a very uniform single chain construct. Also the extended portion (ESGK (SEQ ID NO:2)) will generate a space between the peptide and sugar enabling the access of MHCII molecule to the peptide. This conjugate was designed to be target specific (no protein carrier, which triggers protein specific immune response) and this construct contains one order of magnitude more antigenic epitopes per molecule than the highly crosslinked protein conjugates (one peptide per every 10 repeat units of polysaccharide leading to 10-15 glycated peptide epitopes as opposed to one to two epitopes in a protein-polysaccharide conjugate).

Figure 12:
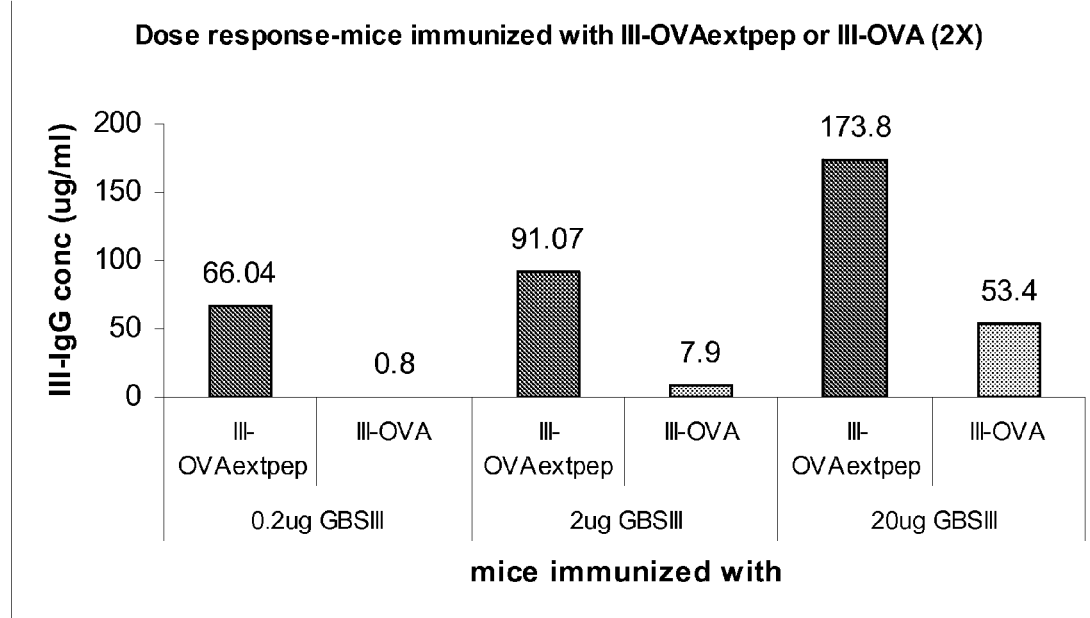
FIG. 12 is a bar graph depicting the results of a dose-response assay for mice immunized with 0.2 μg, 2 μg, or 20 μg of III-OVAextpep or III-OVA.

Four groups of BALB/c (4 mice per group) were immunized three times (days: 0, 14, 28) with: 1) GBSIII alone, 2) OVA, 3) III-OVA, or 4) III-OVAextpep. Sera was obtained from blood collected on day 35. Purified mouse IgG2a monoclonal antibody against GBSIII was used to quantify the GBSIII specific IgG amount in each serum. As shown in FIG. 12, dose-response analysis revealed that mice immunized with III-OVAextpep or III-OVA produced more III-IgG with increasing concentrations of III-OVAextpep and III-OVA.

Figure 11:
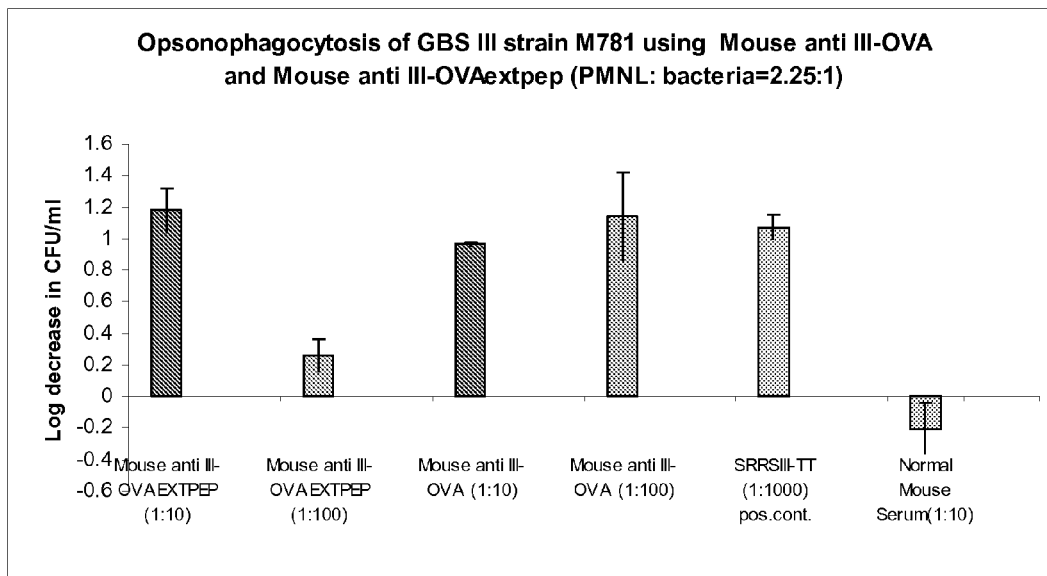
FIG. 11 depicts opsonophagocytosis of type III group B *Streptococcus* by human blood PMNLs, in the presence of serum from mice immunized with III-OVA and III-OVAext-pep. Normal mouse serum and rabbit serum from GBSIII-TT immunized mice were used as controls.

The capacity of III-OVAextpep to induce secretion of GBSIII specific IgG antibodies suggested that this vaccine could be potent in inducing the phagocytosis of type III group B *Streptococcus* by polymorphonuclear leukocytes (PMNLs). To test this, an Opsonophagocytosis Assay was performed using the serum of mice immunized with III-OVAextpep. As shown in FIG. 11, serum from III-OVA extpep immunized mice was as potent as the serum from III-OVA immunized mice in opsonising the bugs to enable their phagocytosis. Knowing that serum from III-OVA extpep immunized mice contains ~7 fold less GBSIII specific IgGs than serum from III-OVA immunized mice; the ability of III-OVAextpep serum to induce opsonophagocytosis is more significant than III-OVA serum.

Figure 13:
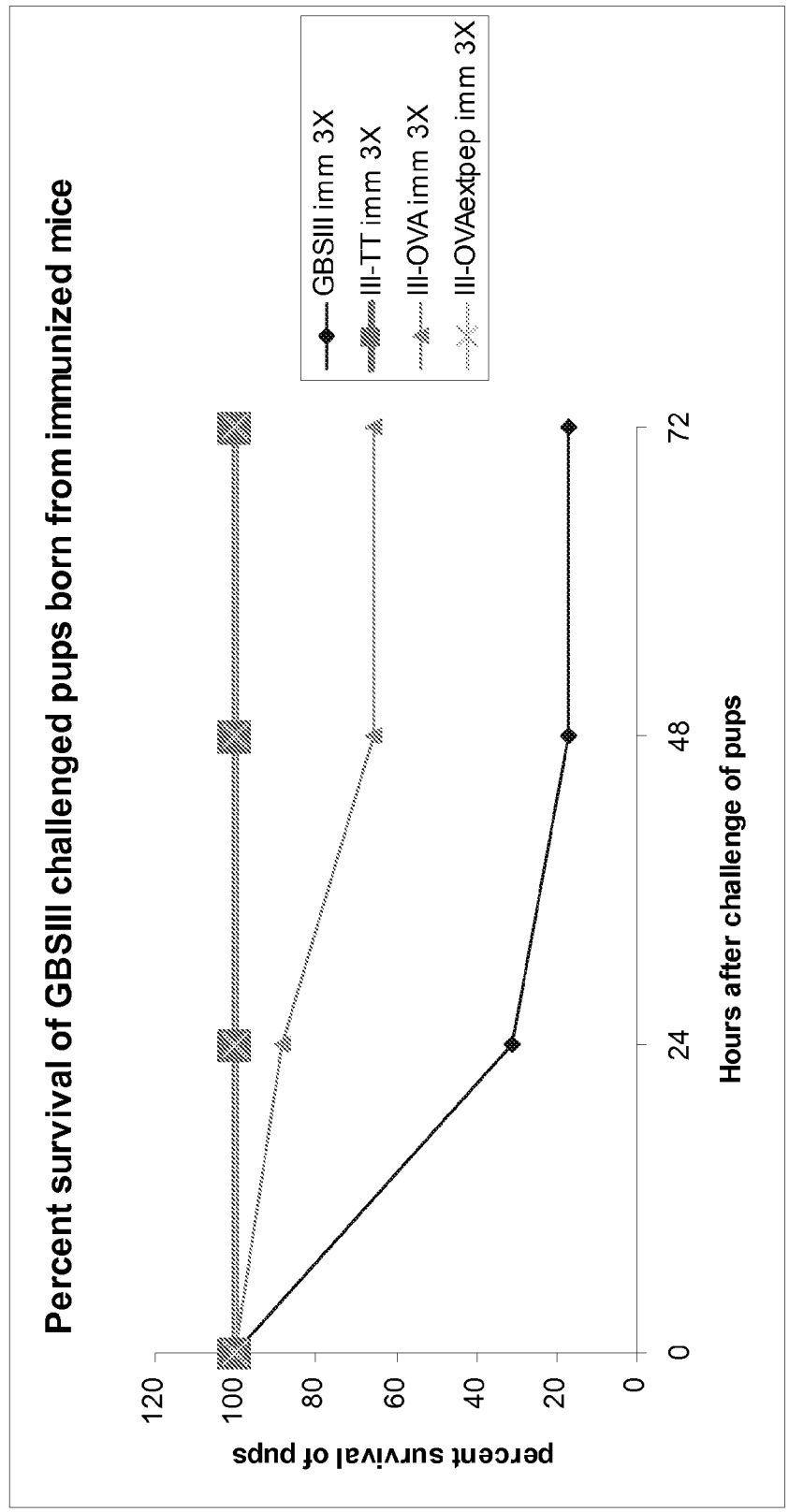
FIG. 13 is a line graph depicting percent survival of pups born to mothers immunized with III-TT, III-OVA, or III-OVAextpep and challenged with type III group B *Streptococcus* (GBSIII).

Neonatal mouse protection assays were performed to examine the protection capacity of III-OVAextpep. Female mice were immunized with III-OVAextpep, GBSIII specific IgG antibodies pass through placenta to the fetus when these immunized female mice are impregnated. Then the pups were challenged with type III group B *Streptococcus*. Percent survival of GSBIII challenged pups was determined at 0, 24, 48, and 72 hours post-challenge. As shown in FIG. 13, survival of the pups that born from the III-OVAextpep immunized mother demonstrated that III-OVAextpep has the capacity to protect mice against GBSIII challenge.

Example 10

In Vivo Priming Assays

To determine whether recognition of the carbohydrate portion of the glycated peptide by CD4+ T cells is a major factor in induction of the humoral immune response to the glycoconjugate, BALB/c mice were primed with GBSIII-OVA and boosted with either GBSIIIOVA or GBSIII-TT. Serum levels of GBSIII-specific IgG were measured (FIG. 14). Three groups of mice served as controls: (1) mice primed and boosted with GBSIII-TT, (2) mice primed with GBSIII and boosted with GBSIII-TT, and (3) mice primed with GBSIII-OVA and boosted with GBSIII. It has been presumed that peptide recognition by CD4+ helper T cells triggers polysaccharide-specific IgG secretion by B cells. Therefore, mice primed and boosted with GBSIII-OVA might have been expected to develop higher titers of serum IgG to GBSIII than mice primed with GBSIII-OVA and boosted with GBSIII-TT. That is, priming and boosting with the same carrier protein would presumably elicit significantly more T-cell help than boosting with a heterologous carrier because of T-cell memory for the peptide from the priming carrier protein. Alternatively, in the setting of T-cell memory for the carbohydrate portion of the glycated peptide, GBSIII-specific IgG titers would not depend upon boosting with the same carrier protein in the conjugate. As is shown in FIG. 14A, boosting of GBSIII-OVA-primed mice with GBSIII-TT induced similar GBSIII-specific IgG secretion as priming and boosting with GBSIII-OVA (p>0.05, ns). This result indicates that T-cells help to induce carbohydrate-specific immune responses is recruited via carbohydrate recognition, not peptide recognition. GBSIII-specific IgG titers after priming are shown in FIG. 14B.

Example 11

Non-Peptide Carrier Moieties

In these experiments, the MHC binding moiety is a zwitterionic carbohydrate, i.e., polysaccharide A (PSA). The PSA has a zwitterionic charge and binds to MHCII. The polysaccharide or oligosaccharide that is to be the target of the induced immune response is coupled to this carrier molecule. The PSA carrier serves in place of the peptide as the anchor to bind to MHCII and the target polysaccharide or oligosaccharide is then available for recognition by the T cell receptor in a manner similar to that for the glycated peptides described in this application. These glycated carrier molecules induce T cell responses required for helper function and antibody production.

Zwitterionic heparosan (*E. coli* K5 polysaccharide, see FIG. 15A) oligosaccharide derivatives were assayed for CD4+ T cell stimulation). A zwitterionic heparosan oligosaccharide was conjugated to a T cell independent antigen to enable its presentation to T cells through the binding of carrier to the MHCII molecule. Human T cell assay performed for the zwitterionic heparosan oligosaccharides. T cell count for SEA antigen (positive control) was normalized to 100. The oligosaccharides were 4 µg/ml. T cell stimulation was measured over 8 days.

Figure 15B:
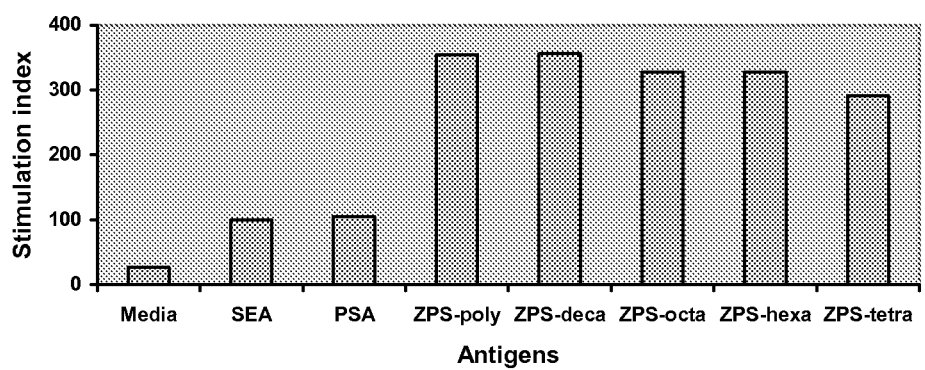
FIG. 15B is a bar graph showing the results of human T cell assays performed for the zwitterionic heparosan oligosaccharides. T cell count for SEA antigen (positive control) was normalized to 100. The oligosaccharides were 4 μg/ml. T cell stimulation was measured over 8 days.

As shown in FIG. 15B, these constructs induced extremely high T cell proliferation.

ADDITIONAL REFERENCES

1. Baumann, H., Tzianabos, A. O., Brisson, J. R., Kasper, D. L., and Jennings, H. J. *Structural elucidation of two capsular polysaccharides from one strain of Bacteroides fragilis using high-resolution NMR spectroscopy*. Biochemistry, 1992. 31(16): p. 4081-4089.
2. Borriello, F., Sethna, M. P., Boyd, S. D., Schweitzer, A. N., Tivol, E. A., Jacoby, D., Strom, T. B., Simpson, E. M., Freeman, G. J., and Sharpe, A. H. *B7-1 and B7-2 have overlapping, critical roles in immunoglobulin class switching and germinal center formation*. Immunity, 1997. 6: p. 303-313.
3. Brubaker, J. O., Li, Q., Tzianabos, A. O., Kasper, D. L., and Finberg, R. W. *Mitogenic activity of purified capsular polysaccharide A from Bacteroides fragilis: differential stimulatory effect on mouse and rat lymphocytes in vitro*. J Immunol, 1999. 162(4): p. 2235-2242.
4. Cobb, B. A., and Kasper, D. L. *Zwitterionic capsular polysaccharides: the new MHCII-dependent antigens*. Cell Microbiol, 2005. 7: p. 1398-1403.
5. Coutinho, A., and Moller, G. *B cell mitogenic properties of thymus-independent antigens*. Nature New Biol, 1973. 245: p. 12-14.
6. Foy, T. M., Shepherd, D. M., Durie, F. H., Aruffo, A., Ledbetter, J. A.,
and Noelle, R. J. *In vivo CD40-gp39 interactions are essential for thymus-dependent humoral immunity. II. Prolonged suppression of the humoral immune response by an antibody to the ligand for CD40, gp39*. J Exp Med, 1993. 178: p. 1567-1575.
7. Guttermsen, H.-K., Wetzler, L. M., Finberg, R. W., and Kasper, D. L. *Immunologic memory induced by a glycoconjugate vaccine in a murine adoptive lymphocyte transfer model*. Infect Immun, 1998. 66: p. 2026-2032.
8. Janeway, C. A., Travers, P., Walport, M., and Chlomchik, M. *Immunobiology, 6th edition.*, Garland Science Publishing: New York. 2005. p.
9. Jennings, H. J., Lugowski, C., and Kasper, D. L. *Conformational aspects critical to the immmunospecificity of the type III group B streptococcal polysaccharide*. Biochemistry, 1981. 20: p. 4511-4518.
10. Jennings, H. J., Rosell, K.-G., and Kasper, D. L. *Structural determination and serology of the native polysaccharide antigen of type III Group B Streptococcus*. Can J Biochem, 1980. 58: p. 112-120.
11. Kasper, D. L., Paoletti, L. C., Wessels, M. R., Guttormsen, H.-K., Carey, V. J., Jennings, H. J., and Baker, C. J. *Immune response to type III group B streptococcal polysaccharide-tetanus toxoid conjugate vaccine*. J Clin Invest, 1996. 98: p. 2308-2314.
12. Kayabe, T., Naka, T., Yoshida, K., Tanaka, T., Fujiwara, H., Suematsu, S., Yoshida, N., Kishimoto, T., and Kikutani, H. *The immune responses in CD40-deficient mice: impaired immunoglobulin class switching and germinal center formation*. Immunity, 1994. 1: p. 167-178.
13. Krinos, C. M., Coyne, M. J., Weinacht, K. G., Tzianabos, A. O., Kasper, D. L., and Comstock, L. E. *Extensive surface diversity of a commensal microorganism by multiple DNA inversions*. Nature, 2001. 414(6863): p. 555-558.

14. Kroll-Amir, H., Nussbaum, G., and Cohen, I. R. *Proteins and their derived peptides as carriers in a conjugate vaccine for streptococcus pneumoniae: self-heat shock protein 60 and tetanus toxoid.* J Immunol, 2003. 170: p. 6165-6171.
15. Mitchison, N. *The carrier effect in the secondary response to hapton-protein conjugates. II. Cellular cooperation.* Eur J Immunol, 1971. 1: p. 18-25.
16. Paoletti, L. C., and Kasper, D. L. *Glycoconjugate vaccines to prevent group B streptococcal infections.* Expert Opin Biol Ther, 2003. 3: p. 975-984.
17. Paoletti, L. C., Wessels, M. R., Michon, F., DiFabio, J. L., Jennings, H. J., and Kasper, D. L. *Group B Streptococcus type II polysaccharide-tetanus toxoid conjugate vaccine.* Infect Immun, 1992. 60: p. 4009-4014.
18. Paoletti, L. C., Wessels, M. R., Rodewald, A. K., Shroff, A. A., Jennings, H. J., and Kasper, D. L. *Neonatal mouse protection against infection with multiple group B streptococcal serotypes by maternal immunization with a tetravalent GBS polysaccharide-tetanus toxoid conjugate vaccine* Infect Immun, 1994. 62: p. 3236-3243.
19. Perez-Melgosa M, Ochs H D, S, L. P., D, L. J., M, v. M., A, F. R., K, E. R., I, M. S., and B, W. C. *Carrier-mediated enhancement of cognate T cell help: the basis for enhanced immunogenicity of meningococcal outer membrane protein polysaccharide conjugate vaccine.* Eur J Immunol, 2001. 31: p. 2373-2381.
20. Petersson, K., Forsberg, G., and Walse, B. *Interplay between superantigens and immunoreceptors.* Scand J Immunol, 2004. 59: p. 345-355.
21. Renshaw, B. R., Fanslow, I., W. C., Armitage, R. J., Campbell, K. A., Liggitt, D., Wright, B., Davison, B. L., and Maliszewski, C. R. *Humoral immune response in the CD40 ligand-deficient mice.* J Exp Med, 1994. 180: p. 1889-1900.
22. Rice, R. H., and Means, G. E. *Radioactive labeling of proteins in vitro.* J Biol Chem, 1971. 246: p. 831-832.
23. Tsuji, M., Romero, P., Nussenzweig, R. S., and Zavala, F. *CD4+ cytolytic T cell clone confers protection against murine malaria.* J Exp Med, 1990. 172: p. 1353-1357.
24. Tzianabos, A. O., Onderdonk, A. B., and Kasper, D. L. *Bacterial structure and functional relation to abscess formation.* Infect Agents Dis, 1994. 3(5): p. 256-265.
25. Tzianabos, A. O., Onderdonk, A. B., Rosner, B., Cisneros, R. L., and Kasper, D. L. *Structural features of polysaccharides that induce intra-abdominal abscesses.* Science, 1993. 262: p. 416-419.
26. Tzianabos, A. O., Onderdonk, A. B., Smith, R. S., and Kasper, D. L. *Structure-function relationships for polysaccharide-induced intra-abdominal abscesses.* Infect Immun, 1994. 62(8): p. 3590-3593.
27. Valmori, D., Pessi, A., Bianchi, E., and Corradin, G. *Use of human universally antigenic tetanus toxin T cell epitopes as carriers for human vaccination.* J Immunol, 1992. 149: p. 717-721.
28. Viret, C., and Janeway, C. A., Jr. *MHC and T cell development.* Rev Immunogenet, 1999. 1: p. 91-104.
29. Wessels, M. R., DiFabio, J. L., Benedi, V. J., Kasper, D. L., Michon, F., Brisson, J. R., Jelinkova, J., and Jennings, H. J. *Structural determination and immunochemical characterization of the type V group B Streptococcus capsular polysaccharide.* J Biol Chem, 1991. 266: p. 6714-6719.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of preparing a glycated peptide conjugate, the method comprising:
    obtaining a population of polysaccharides;
    treating the population of polysaccharides to create a treated population of polysaccharides having an average molecular weight of 10-20 kDa;
    contacting the treated population of polysaccharides with polypeptides comprising a plurality of repeating peptide units linked together by cleavable moieties, wherein each peptide unit consists of:
    (i) an MHC-II binding sequence of 20 amino acids or fewer, wherein none of the amino acids are lysine;
    (ii) one lysine residue at the C terminal end; and
    (iii) one or more amino acids linking the MHC-II binding sequence to the lysine residue, wherein none of the amino acids are lysine;
    under conditions sufficient to link the treated polysaccharides directly to the lysine residues, thereby preparing the glycated peptide conjugate.

2. The method of claim 1, further comprising:
    providing a biocompatible nanoparticle; and
    linking the N terminal end of the glycated peptide conjugate to the biocompatible nanoparticle via a cleavable linker.

3. The method of claim 1, wherein the population of polysaccharides is from a pathogen selected from the group consisting of viruses, bacteria, protozoa, and fungi.

4. The method of claim 1, wherein the population of polysaccharides is from a tumor.

5. The method of claim 1, wherein treating the population of polysaccharides comprises exposing the polysaccharide to ozonolysis or enzymatic digestion.

6. The method of claim 2, wherein the cleavable linker is an acid-labile sequence.

7. The method of claim 2, wherein the cleavable linker is a protease recognition sequence.

8. The method of claim 1, wherein the glycated peptide conjugate comprises peptide units with the same MHC-II binding sequence.

9. The method of claim 1, wherein the glycated peptide conjugate comprises peptide units with different MHC-II binding sequences.

10. A glycated peptide conjugate comprising a polypeptide comprising a plurality of repeating peptide units linked together by cleavable moieties, wherein each peptide unit consists of:
    (i) an MHC-II binding sequence of 20 amino acids or fewer, wherein none of the amino acids are lysine;
    (ii) one lysine residue at the C terminal end;
    (iii) one or more amino acids linking the MHC-II binding sequence to the lysine residue, wherein none of the amino acids are lysine; and
    (iv) a polysaccharide having an average molecular weight of 10-20 kDa linked directly to the lysine residue.

11. The glycated peptide conjugate of claim 10, wherein the glycated peptide conjugate is linked to a biocompatible nanoparticle at the N terminal end of the glycated peptide conjugate, via a cleavable linker.

12. The glycated peptide conjugate of claim 10, wherein the polysaccharide is from a pathogen selected from the group consisting of viruses, bacteria, protozoa, and fungi.

13. The glycated peptide conjugate of claim 10, wherein the polysaccharide is from a tumor.

14. The glycated peptide conjugate of claim 10, wherein the cleavable moiety is an acid-labile sequence.

15. The glycated peptide conjugate of claim 10, wherein the cleavable moiety is a protease recognition sequence.

16. The glycated peptide conjugate of claim 10, wherein the plurality of peptide units comprise the same MHC-II binding sequence.

17. The glycated peptide conjugate of claim 10, wherein the plurality of peptide units comprise a plurality of MHC-II binding sequences.

18. A method of inducing an immune response in a subject, the method comprising administering a therapeutically effective amount of the glycated peptide conjugate of claim 10.

19. A composition comprising the glycated peptide conjugate of claim 10, in a pharmaceutically acceptable carrier.

20. A glycated peptide conjugate comprising a peptide unit consisting of:
    (i) an MHC-II binding sequence of 20 amino acids or fewer, wherein none of the amino acids are lysine;
    (ii) a lysine residue at the C terminal end;
    (iii) one or more amino acids linking the MHC-II binding sequence to the lysine residue, wherein none of the amino acids are lysine; and
    (iv) a polysaccharide having an average molecular weight of 10-20 kDa linked directly to the lysine residue.

21. The glycated peptide conjugate of claim 20, wherein the glycated peptide conjugate is linked to a biocompatible nanoparticle at the N terminal end of the glycated peptide conjugate, via a cleavable linker.

22. The glycated peptide conjugate of claim 20, wherein the polysaccharide is from a pathogen selected from the group consisting of viruses, bacteria, protozoa, and fungi.

23. The glycated peptide conjugate of claim 20, wherein the polysaccharide is from a tumor.

24. The method of claim 21, wherein the cleavable linker is an acid-labile sequence.

25. The method of claim 21, wherein the cleavable linker is a protease recognition sequence.

26. A method of inducing an immune response in a subject, the method comprising administering a therapeutically effective amount of the glycated peptide conjugate of claim 20.

27. A composition comprising the glycated peptide conjugate of claim 20, in a pharmaceutically acceptable carrier.

28. The glycated peptide conjugate of claim 10, wherein the one or more amino acids linking the MHC-II binding sequence to the lysine residue comprise an amino acid sequence of glutamate-serine-glycine.

29. The glycated peptide conjugate of claim 10, wherein the polysaccharide has an average molecular weight of 10-15 kDa.

30. The glycated peptide conjugate of claim 10, wherein the polysaccharide has an average molecular weight of 10 kDa.

31. The glycated peptide conjugate of claim 10, wherein the polysaccharide has an average molecular weight of 15 kDa.

32. The glycated peptide conjugate of claim 20, wherein the one or more amino acids linking the MHC-II binding sequence to the lysine residue comprise an amino acid sequence of glutamate-serine-glycine.

33. The glycated peptide conjugate of claim 20, wherein the polysaccharide has an average molecular weight of 10-15 kDa.

34. The glycated peptide conjugate of claim 20, wherein the polysaccharide has an average molecular weight of 10 kDa.

35. The glycated peptide conjugate of claim 20, wherein the polysaccharides have polysaccharide has an average molecular weight of 15 kDa.

36. The method of claim 1, wherein the cleavable moiety is an acid-labile sequence.

37. The method of claim 1, wherein the cleavable moiety is a protease recognition sequence.

38. The method of claim 4, wherein the polysaccharide is from a glycoprotein selected from the group consisting of Mucin-1 (MUC-1), NER-2/neu, carcino-embryonic antigen (CEA), p53, Sialyl Tn (STn), Globo H, GM2 ganglioside, GD2 ganglioside, and GD3 ganglioside.

39. The method of claim 11, wherein the cleavable linker is an acid-labile sequence.

40. The method of claim 11, wherein the cleavable linker is a protease recognition sequence.

41. The glycated peptide conjugate of claim 13, wherein the polysaccharide is from a glycoprotein selected from the group consisting of Mucin-1 (MUC-1), NER-2/neu, carcino-embryonic antigen (CEA), p53, Sialyl Tn (STn), Globo H, GM2 ganglioside, GD2 ganglioside, and GD3 ganglioside.

42. The glycated peptide conjugate of claim 23, wherein the polysaccharide is Mucin-1 (MUC-1), NER-2/neu, carcino-embryonic antigen (CEA), p53, Sialyl Tn (STn), Globo H, GM2 ganglioside, GD2 ganglioside, or GD3 ganglioside.

* * * * *

SEQUENCE LISTING

```
<160> NUMBER OF SEQ ID NOS: 2

<210> SEQ ID NO 1
<211> LENGTH: 21
<212> TYPE: PRT
<213> ORGANISM: Artificial Sequence
<220> FEATURE:
<223> OTHER INFORMATION: synthetically generated peptide fragment of
      ovalbumin

<400> SEQUENCE: 1

Ile Ser Gln Ala Val His Ala Ala His Ala Glu Ile Asn Glu Ala Gly
1               5                   10                  15

Arg Glu Ser Gly Lys
            20

<210> SEQ ID NO 2
<211> LENGTH: 4
<212> TYPE: PRT
<213> ORGANISM: Artificial Sequence
<220> FEATURE:
<223> OTHER INFORMATION: synthetically generated peptide fragment

<400> SEQUENCE: 2

Glu Ser Gly Lys
1
```